US011864944B2

(12) United States Patent
Fornwalt et al.

(10) Patent No.: US 11,864,944 B2
(45) Date of Patent: Jan. 9, 2024

(54) SYSTEMS AND METHODS FOR A DEEP NEURAL NETWORK TO ENHANCE PREDICTION OF PATIENT ENDPOINTS USING VIDEOS OF THE HEART

(71) Applicant: Geisinger Clinic, Danville, PA (US)

(72) Inventors: Brandon K. Fornwalt, Lewisburg, PA (US); Christopher Haggerty, Lewisburg, PA (US); Alvaro Ulloa Cerna, Danville, PA (US); Christopher Good, Fairview, PA (US)

(73) Assignee: Geisinger Clinic, Danville, PA (US)

( * ) Notice: Subject to any disclaimer, the term of this patent is extended or adjusted under 35 U.S.C. 154(b) by 534 days.

(21) Appl. No.: 17/099,743

(22) Filed: Nov. 16, 2020

(65) Prior Publication Data

US 2021/0145404 A1 May 20, 2021

Related U.S. Application Data

(60) Provisional application No. 62/936,377, filed on Nov. 15, 2019.

(51) Int. Cl.
*A61B 8/08* (2006.01)
*G16H 50/20* (2018.01)
(Continued)

(52) U.S. Cl.
CPC .............. *A61B 8/0883* (2013.01); *A61B 8/04* (2013.01); *A61B 8/065* (2013.01); *A61B 8/14* (2013.01); *A61B 8/5223* (2013.01); *A61B 8/5246* (2013.01); *A61B 8/5292* (2013.01); *G06N 3/045* (2023.01); *G06N 3/08* (2013.01); *G06T 7/0002* (2013.01); *G06T 7/0012* (2013.01);
(Continued)

(58) Field of Classification Search
CPC ...... A61B 8/0883; G16H 20/40; G16H 70/60; G16H 10/40; G16H 10/60; G16H 50/30; G16H 50/70; G16H 50/20
See application file for complete search history.

(56) References Cited

U.S. PATENT DOCUMENTS

2010/0057490 A1 3/2010 Kocis et al.
2016/0203287 A1 7/2016 Chen et al.
(Continued)

FOREIGN PATENT DOCUMENTS

WO 2019153039 A1 8/2019

OTHER PUBLICATIONS

Large Scale Electronic Health Record Data and Echocardiography Video Analysis for Mortality Risk Prediction (Year: 2019).*
(Continued)

*Primary Examiner* — Joel F Brutus
(74) *Attorney, Agent, or Firm* — Quarles & Brady LLP

(57) ABSTRACT

A method for determining a predicted risk level of a clinical endpoint for a predetermined time period for a patient is provided by the present disclosure. The method includes receiving video frames of a heart, the video frames being associated with the patient, receiving electronic health record data including a number of variables associated with the patient, providing the video frames and the electronic health record data to the trained neural network, receiving a risk score from the trained neural network, and outputting a report based on the risk score to at least one of a display or a memory.

30 Claims, 20 Drawing Sheets

(51) Int. Cl.
| | |
|---|---|
| G16H 50/30 | (2018.01) |
| G16H 30/40 | (2018.01) |
| G16H 15/00 | (2018.01) |
| G16H 50/70 | (2018.01) |
| G16H 70/60 | (2018.01) |
| G16H 30/20 | (2018.01) |
| G16H 10/40 | (2018.01) |
| G16H 20/40 | (2018.01) |
| G06T 7/00 | (2017.01) |
| A61B 8/14 | (2006.01) |
| G16H 10/60 | (2018.01) |
| A61B 8/04 | (2006.01) |
| A61B 8/06 | (2006.01) |
| G06N 3/08 | (2023.01) |
| G06N 3/045 | (2023.01) |

(52) U.S. Cl.
CPC ............ *G16H 10/40* (2018.01); *G16H 10/60* (2018.01); *G16H 15/00* (2018.01); *G16H 20/40* (2018.01); *G16H 30/20* (2018.01); *G16H 30/40* (2018.01); *G16H 50/20* (2018.01); *G16H 50/30* (2018.01); *G16H 50/70* (2018.01); *G16H 70/60* (2018.01); *G06T 2207/10016* (2013.01); *G06T 2207/20081* (2013.01); *G06T 2207/20084* (2013.01); *G06T 2207/30048* (2013.01)

(56) References Cited

U.S. PATENT DOCUMENTS

| | | |
|---|---|---|
| 2018/0005130 A1 | 1/2018 | Dong et al. |
| 2018/0108125 A1 | 4/2018 | Beymer et al. |

OTHER PUBLICATIONS

Payne, J. W. Task complexity and contingent processing in decision making: An information search and protocol analysis. Organ. Behav. Hum. Perform. 16, 366-387 (1976).
Prechelt, L. in Neural Networks: Tricks of the Trade (eds Montavon, G. et al.) 53-67 (Springer, 1998).
Quer, G., et al. Augmenting diagnostic vision with AI. Lancet 390, 221 (2017).
Raghunath, S. et al. Prediction of mortality from 12-lead electrocardiogram voltage data using a deep neural network. Nat. Med. 26, 886-891 (2020).
Rajkomar, A. et al. Scalable and accurate deep learning with electronic health records. npj Digit. Med. 1, 18 (2018).
Rudin, C. Stop explaining black box machine learning models for high stakes decisions and use interpretable models Instead. Nat. Mach. Intell. 1, 206-215 (2019).
Samad, M. D. et al. Predicting Survival From Large Echocardiography and Electronic Health Record Datasets. JACC Cardiovasc Imaging. Apr. 2019 ; 12(4): 681-689.
Setio, A. A. A. et al. Pulmonary nodule detection in CT images: false positive reduction using multi-view convolutional networks. IEEE Trans. Med. Imaging 35, 1160-1169 (2016).
Simonyan, K. et al. Two-Stream Convolutional Networks for Action Recognition in Videos. arXiv Prepr. arXiv1406.2199 9905, 1-11 (2016).
Srivastava, N., et al. Dropout: a simple way to prevent neural networks from overfitting. J. Mach. Learn. Res. 15, 1929-1958 (2014).
Szegedy, C., et al. Rethinking the inception architecture for computer vision. In Proc. IEEE Conference on Computer Vision and Pattern Recognition 2818-2826 (2016).
Tran, D., et al. Learning spatiotemporal features with 3D convolutional networks. In Proc. IEEE International Conference on Computer Vision 4489-4497 (2015).
Ulloa, A., et al. "A deep neural network to enhance prediction of 1-year mortality using echocardiographic videos of the heart." arXiv preprint arXiv:1811.10553 (2018).
Van Buuren, S. et al. MICE: multivariate imputation by chained equations in R. J. Stat. Softw. 45, jss.v045.i03 (2011).
Van Woudenberg, N. et al. in Simulation, Image Processing, and Ultrasound Systems for Assisted Diagnosis and Navigation (eds Stoyanov, D. et al.) 74-81 (Springer, 2018).
Venugopalan, S. et al. Sequence to sequence—Video to text. Proc. IEEE Int. Conf. Comput. Vis. 2015 Inter, 4534-4542 (2015).
Venugopalan, S. et al. Translating videos to natural language using deep recurrent neural networks. In Proceedings of the 2015 Conference of the North American Chapter of the Association for Computational Linguistics: Human Language Technologies (Association for Computational Linguistics, 2015).
Wehner, G. J. et al. Routinely reported ejection fraction and mortality in clinical practice: where does the nadir of risk lie? Eur. Heart J. 41, 1249-1257 (2020).
White, I. R., et al. Multiple imputation using chained equations: issues and guidance for practice. Stat. Med. 30, 377-399 (2011).
Williams, B. A. et al. Applying the Seattle Heart Failure model in the office setting in the era of electronic medical records. Circ. J. 82, 724-731 (2018).
Yadlowsky, S. et al. Clinical implications of revised pooled cohort equations for estimating atherosclerotic cardiovascular disease risk. Ann. Intern. Med. 169, 20-29 (2018).
Yancy, C. W. et al. 2013 ACCF/AHA guideline for the management of heart failure: a report of the American College of Cardiology Foundation/American Heart Association Task Force on Practice Guidelines. J. Am. Coll. Cardiol. 62, e147-e239 (2013).
Zhang, J. et al. Fully Automated Echocardiogram Interpretation in Clinical Practice. Circulation 138, 1623-1635 (2018).
Arbabshirani, M. R. et al. Advanced machine learning in action: identification of intracranial hemorrhage on computed tomography scans of the head with clinical workflow integration. npj Digit. Med. 1, 9 (2018).
Arcadu, F. et al. Deep learning algorithm predicts diabetic retinopathy progression in individual patients. npj Digit. Med. 2, 92 (2019).
Avati, A. et al. Improving palliative care with deep learning. BMC Med. Inform. Decis. Mak. 18, 122 (2018).
Behnami, D. et al. Automatic cine-based detection of patients at high risk of heart failure with reduced ejection fraction in echocardiograms. Comput. Methods Biomech. Biomed. Eng. Imaging Vis. https://doi.org/10.1080/21681163.2019.1650398 (2019).
Behnami, D. et al. Dual-view joint estimation of left ventricular ejection fraction with uncertainty modelling in echocardiograms. In International Conference on Medical Image Computing and Computer-Assisted Intervention (eds Shen, D et al.) 696-704 (Springer, 2019).
Chen, T. et al. Xgboost: a scalable tree boosting system. In Proc. 22nd ACM SIGKDD International Conference on Knowledge Discovery and Data Mining 785-794 (ACM, 2016).
Chesebro, J. H. et al. Thrombolysis in myocardial infarction (TIMI) trial, phase I: A comparison between intravenous tissue plasminogen activator and intravenous streptokinase. Clinical findings through hospital discharge. Circulation (1987).
Cui, X. et al. Deformable regions of interest with multiple points for tissue tracking in echocardiography. Med. Image Anal. 35, 554-569 (2017).
Dauphin, Y. N., et al. Equilibrated adaptive learning rates for nonconvex optimization. in Advances in Neural Information Processing Systems 28 1504-1512 (2015). doi: 10.1016/B978-0-12-385235-9.00003-5.
Donahue, J. et al. Long-Term Recurrent Convolutional Networks for Visual Recognition and Description. IEEE Trans. Pattern Anal. Mach. Intell. 39, 677-691 (2017). DOI: 10.1109/TPAMI.2016.2599174.
Dou, Q. et al. Automatic detection of cerebral microbleeds from MR images via 3D convolutional neural networks. IEEE Trans. Med. Imaging 35, 1182-1195 (2016).
Duchi, J., et al. Adaptive subgradient methods for online learning and stochastic optimization. in The Journal of Machine Learning Research 12, 2121-2159 (2011).

(56) References Cited

OTHER PUBLICATIONS

Eagle, K. A. et al. A Validated Prediction Model for All Forms of Acute Coronary Syndrome. JAMA (2004). doi:10.1001/jama.291.22.2727.
Esteva, A. et al. Dermatologist-level classification of skin cancer with deep neural networks. Nature 542, 115-118 (2017).
Gahungu, N., et al. Current challenges and recent updates in artificial intelligence and echocardiography. Curr. Cardiovasc. Imaging Rep. 13, 5 (2020).
Ge, R. et al. Echoquan-net: direct quantification of echo sequence for left ventricle multidimensional indices via global—local learning, geometric adjustment and multi-target relation learning. In International Conference on Artificial Neural Networks (eds Tetko, I. et al.) 219-230 (Springer, 2019).
Ge, R. et al. K-net: Integrate left ventricle segmentation and direct quantification of paired echo sequence. IEEE Trans. Med. imaging 39, 1690-1702 (2019).
Ghorbani, A. et al. Deep learning interpretation of echocardiograms. npj Digit. Med. 3, 10 (2020).
Greff, K., et al. LSTM: A Search Space Odyssey. IEEE Trans. Neural Networks Learn. Syst. 28, 2222-2232 (2017).
Gulshan, V. et al. Development and validation of a deep learning algorithm for detection of diabetic retinopathy in retinal fundus photographs. JAMA 316, 2402-2410 (2016).
Hadamitzky, M. et al. Optimized prognostic score for coronary computed tomographic angiography: Results from the CONFIRM registry (COronary CT angiography evaluation for clinical outcomes: An international multicenter registry). J. Am. Coll. Cardiol. 62, 468-476 (2013).
He, K., et al. Delving deep into rectifiers: Surpassing human-level performance on imagenet classification. Proc. IEEE Int. Conf. Comput. Vis. 2015 Inter, 1026-1034 (2015).
Hochreiter, S. et al. Long short-term memory. Neural Comput. 9, 1-32 (1997).
Horgan, S. J. et al. in Essential Echocardiography: A Companion to Braunwald's Heart Disease (eds Solomon, S. D. et al.) 460-473 (Elsevier, 2019).
Huang, G., et al. Densely connected convolutional networks. In Proc. IEEE Conference on Computer Vision and Pattern Recognition 4700-4708 (2017).
International Searching Authority. International Search Report and Written Opinion for application PCT/US2020/060800. dated Feb. 19, 2021. 9 pages.
Jafari, M. H. et al. Automatic biplane left ventricular ejection fraction estimation with mobile point-of-care ultrasound using multi-task learning and adversarial training. Int. J. Comput. Assist. Radiol. Surg. 14, 1027-1037 (2019).
Jha, S. et al. Adapting to Artificial Intelligence: Radiologists and Pathologists as Information Specialists. JAMA 316, 2353-2354 (2016).
Ji, S., et al. 3D convolutional neural networks for human action recognition. IEEE Trans. Pattern Anal. Mach. Intell. 35, 221-231 (2012).
Jing, L. et al. A machine learning approach to management of heart failure populations. JACC Heart Fail. 8, 578-587 (2020).
Karpathy, A. et al. Large-Scale Video Classification with Convolutional Neural Networks. in 2014 IEEE Conference on Computer Vision and Pattern Recognition 1725-1732 (IEEE, 2014).
Kavalieratos, D. et al. Palliative care in heart failure: rationale, evidence, and future priorities. J. Am. Coll. Cardiol. 70, 1919-1930 (2017).
Kenchaiah, S. et al. Obesity and the Risk of Heart Failure. N. Engl. J. Med. 347, 305-313 (2002).
Kennedy, E. H., et al. Improved cardiovascular risk prediction using nonparametric regression and electronic health record data. Med. Care 51, 251-8 (2013).
Kusunose, K. et al. A deep learning approach for assessment of regional wall motion abnormality from echocardiographic images. JACC Cardiovasc. Imagin 13, 374-381 (2019).
Kwon, J.-m, et al. Deep learning for predicting in-hospital mortality among heart disease patients based on echocardiography. Echocardiography 36, 213-218 (2019).
Kyriacou, E., et al. in Biomedical Signals, Imaging, and Informatics 4th edn (eds Bronzino, J. D. & Peterson, D.) Ch. 64 (CRC Press, 2015).
Lang, R. M. et al. Recommendations for Cardiac Chamber Quantification by Echocardiography in Adults: An Update from the American Society of Echocardiography and the European Association of Cardiovascular Imaging. J. Am. Soc. Echocardiogr. 28, 1-39.e14 (2015).
Lecun, Y. et al. Deep learning. Nature 521, 436-444 (2015).
Lee, H. et al. An explainable deep-learning algorithm for the detection of acute intracranial haemorrhage from small datasets. Nat. Biomed. Eng. 3, 173 (2019).
Levy, W. C. et al. The Seattle Heart Failure model. Circulation 113, 1424-1433 (2006).
Li, M. et al. Unified model for interpreting multi-view echocardiographic sequences without temporal information. Appl. Soft Comput. 88, 106049 (2020).
Liao, Z. et al. On modelling label uncertainty in deep neural networks: automatic estimation of intra-observer variability in 2D echocardiography quality assessment. IEEE Trans. Med. Imaging 39, 1868-1883 (2019).
Lund, L. H., et al. Predicting survival in ambulatory patients with severe heart failure on beta-blocker therapy. Am. J. Cardiol. 92, 1350-1354 (2003).
Madani, A., et al. Deep echocardiography: data-efficient supervised and semi-supervised deep learning towards automated diagnosis of cardiac disease. npj Digit. Med. 1, 59 (2018).
Madani, A., et al. Fast and accurate classification of echocardiograms using deep learning. NPJ Digital Medicine 1 (2018).
McCarty, C. A. et al. The eMERGE network: a consortium of biorepositories linked to electronic medical records data for conducting genomic studies. BMC Med. Genomics 4, 13 (2011).
Motwani, M. et al. Machine learning for prediction of all-cause mortality in patients with suspected coronary artery disease: a 5-year multicentre prospective registry analysis. Eur. Heart J. 38, 500-507 (2016).
Murillo, S. et al. Motion and deformation analysis of ultrasound videos with applications to classification of carotid artery plaques. In SPIE Medical Imaging (SPIE, 2012).
Ouyang, D. et al. Video-based AI for beat-to-beat assessment of cardiac function. Nature 580, 252-256 (2020).

\* cited by examiner

SYSTEMS AND METHODS FOR A DEEP NEURAL NETWORK TO ENHANCE PREDICTION OF PATIENT ENDPOINTS USING VIDEOS OF THE HEART

CROSS-REFERENCE TO RELATED APPLICATIONS

This application claims the benefit of priority to U.S. provisional application 62/936,377, filed Nov. 15, 2019.

BACKGROUND OF THE DISCLOSURE

The present invention relates to systems and methods for analysis of heart anatomy. Imaging is critical to treatment decisions in most modern medical specialties and has also become one of the most data rich components of electronic health records (EHRs). For example, during a single routine ultrasound of the heart (an echocardiogram), approximately 10-50 videos (~3,000 images) are acquired to assess heart anatomy and function. In clinical practice, a cardiologist realistically has 10-20 minutes to interpret these 3,000 images within the context of numerous other data streams such as laboratory values, vital signs, additional imaging studies (radiography, magnetic resonance imaging, nuclear imaging, computed tomography) and other diagnostics (e.g. electrocardiogram). While these numerous sources of data offer the potential for more precise and accurate clinical predictions, humans have limited capacity for data integration in decision making. Hence, there is both a need and a substantial opportunity to leverage technology, such as artificial intelligence and machine learning, to manage this abundance of data and ultimately provide intelligent computer assistance to physicians.

Thus, what is needed is a system for efficiently and accurately analyzing videos of the heart, for example those acquired during an echocardiogram, cardiac magnetic resonance imaging (MRI) or cardiac computed tomography (CT), in order to assist physicians in assessing heart anatomy and function and to provide accurate predictions about future clinical events.

BRIEF SUMMARY OF THE DISCLOSURE

The present disclosure includes systems and methods for efficiently and accurately analyzing videos of the heart in order to assist physicians in assessing heart anatomy and function by providing prognostic assistance. More specifically, the present disclosure provides a neural network capable of receiving echocardiography videos as well as electronic health record (EHR) data and outputting a mortality risk score or level associated with a predicted mortality of a patient.

Some embodiments of the present disclosure provide a method including receiving an echocardiographic video of a heart associated with a patient, providing the echocardiographic video to a trained neural network, the trained neural network being trained to generate a mortality risk score based on input echocardiographic video, receiving a mortality risk score associated with the patient from the trained neural network, and outputting the mortality risk score associated with the patient to at least one of a memory or a display for viewing by a medical practitioner or healthcare administrator.

In the method, the mortality risk score associated with the patient can be indicative of a likelihood the patient will die within a predetermined period of time from when the echocardiographic video was generated. The mortality risk score associated with the patient can be indicative of a likelihood the patient will die from all causes within the predetermined period of time.

In the method, the trained neural network can be trained based on a training dataset including a plurality of videos, each video of the plurality of videos being associated with an echocardiographic view selected from among a number of echocardiographic views, at least a portion of the training dataset being associated with definite heart failure in accordance with cMERGE. The number of echocardiographic views can include at least one echocardiographic view. The number of echocardiographic views can include at least one of an apical two-chamber view, an apical three-chamber view, an apical four-chamber view, an apical four-chamber focused to right ventricle view, an apical five chamber view, a parasternal long axis view, a parasternal long descending aorta view, a parasternal long mitral valve view, a parasternal long pulmonic valve view, a parasternal long right ventricle inflow view, a parasternal long zoom aortic valve view, a parasternal short aortic valve view, a parasternal short pulmonic valve and pulmonary artery view, a parasternal short tricuspid valve view, a short axis apex view, a short axis base view, a short axis mid papillary view, a subcostal four-chamber view, a subcostal hepatic vein view, a subcostal inter-atrial septum view, a subcostal inferior vena cava view, a subcostal right ventricle view, a suprasternal notch view, a short axis mid papillary view, a short axis apex view, an apical three-chamber zoom view, an apical two-chamber zoom view, or a short axis base view. The training dataset further can include a plurality of survival outcomes, each video of the plurality of videos being associated with a survival outcome included in the plurality of survival outcomes. The training dataset can further include an electronic health record dataset, and each video of the plurality of videos can be associated with a portion of the electronic health record dataset. The electronic health record dataset can be associated with a number of patients and can include values of a number of parameters including age, tricuspid regurgitation maximum velocity, heart rate, low density lipoprotein, left ventricular ejection fraction, diastolic pressure, pulmonary artery acceleration time, systolic pressure, pulmonary artery acceleration slope, and diastolic function. The electronic health record dataset can include values of a number of parameters including demographic parameters, vitals parameters, laboratory measurement parameters, echocardiogram-based parameters, and diagnosis parameters. The demographic parameters can include age, sex, and smoking status. The vitals parameters can include height, weight, heart rate, diastolic blood pressure, and systolic blood pressure. The laboratory measurement parameters can include low-density lipoprotein level and high-density lipoprotein level. The echocardiogram-based parameters can include physician-reported left ventricular ejection fraction, aortic insufficiency deceleration slope, aortic insufficiency maximum velocity, velocity-time integral of distal to aortic valve flow, maximum velocity of distal to aortic valve flow, mean velocity of distal to aortic valve flow, aortic root diameter, ascending aortic diameter, Iv end-diastolic volume: apical 2-chamber; modified ellipsoid, Iv end-diastolic volume: apical 4-chamber; modified ellipsoid, Iv end-diastolic volume: apical 2-chamber; single plane, Iv end-diastolic volume: apical 4-chamber; single plane, Iv end-systolic volume: apical 2-chamber; modified ellipsoid, Iv end-systolic volume: apical 4-chamber; modified ellipsoid, Iv end-systolic volume: apical 2-chamber; single plane, Iv end-systolic volume: apical 4-chamber;

single plane, iv septum dimension at end-diastole, left atrium dimension, left atrium volume derived from apical 2-chamber; modified ellipsoid, left atrium volume derived from apical 4-chamber; modified ellipsoid, velocity-time integral proximal to the obstruction, maximum Iv velocity proximal to the obstruction, mean Iv velocity proximal to the obstruction, Iv area at end-diastole derived from apical 2-chamber, Iv area at end-diastole derived from apical 4-chamber, Iv area at end-systole derived from apical 2-chamber, Iv area at end-systole derived from apical 4-chamber, Iv internal dimension at end-diastole, Iv internal dimension at end-systole, Iv long-axis length at end-diastole derived from apical 2-chamber, Iv long-axis length at end-diastole derived from apical 4-chamber, Iv long-axis length at end systole derived from apical 2-chamber, Iv long-axis length at end systole derived from apical 4-chamber, Iv outflow tract area, Iv outflow tract diameter, Iv posterior wall thickness at end-diastole, mitral regurgitation maximum velocity, a-point maximum velocity of mitral flow, e-point maximum velocity of mitral flow, maximum velocity of mitral valve flow, mitral valve deceleration slope, mitral valve deceleration time, maximum velocity of distal to pulmonic valve flow, pulmonary artery acceleration slope, pulmonary artery acceleration time, pulmonary r-r time interval, right atrial end-systolic mean pressure, right ventricle dimension at end-diastole, tricuspid regurgitation maximum velocity, aortic valve regurgitation, mitral valve regurgitation, tricuspid valve regurgitation, pulmonary valve regurgitation, aortic valve stenosis, mitral valve stenosis, tricuspid valve stenosis, pulmonary valve stenosis, and physician-reported diastolic function. The diagnosis parameters can include: diagnosis of acute rheumatic fever, diagnosis of chronic rheumatic heart disease, diagnosis of hypertensive diseases, diagnosis of ischemic heart diseases, diagnosis of pulmonary heart disease and diseases of pulmonary circulation, diagnosis of acute pericarditis, diagnosis of other forms of heart disease, diagnosis of acute myocarditis, diagnosis of cardiomyopathy, diagnosis of cardiac arrest, diagnosis of paroxysmal tachycardia, diagnosis of atrial fibrillation, diagnosis of heart failure, diagnosis of cerebrovascular diseases, diagnosis of diseases of arteries, arterioles and capillaries, diagnosis of diseases of veins, lymphatic vessels, and lymph nodes, diagnosis of hypotension, diagnosis of other and unspecified disorders of the circulatory system, diagnosis of diabetes mellitus, diagnosis of congenital heart defect, diagnosis of dyslipidemia, and diagnosis of chronic kidney disease.

The method can further include receiving electronic health record information associated with the patient, and providing the electronic health record information to the trained neural network, the trained neural network being further trained to generate the mortality risk score based on input electronic health record information. The electronic health record information can include values of a number of parameters including age, tricuspid regurgitation maximum velocity, heart rate, low density lipoprotein, left ventricular ejection fraction, diastolic pressure, pulmonary artery acceleration time, systolic pressure, pulmonary artery acceleration slope, and diastolic function, the values being associated with the patient. The electronic health record information can include values of a number of parameters including demographic parameters, vitals parameters, laboratory measurement parameters, echocardiogram-based parameters, and diagnosis parameters. The demographic parameters can include age, sex, and smoking status. The vitals parameters can include height, weight, heart rate, diastolic blood pressure, and systolic blood pressure. The laboratory measurement parameters can include low-density lipoprotein level and high-density lipoprotein level. The echocardiogram-based parameters can include physician-reported left ventricular ejection fraction, aortic insufficiency deceleration slope, aortic insufficiency maximum velocity, velocity-time integral of distal to aortic valve flow, maximum velocity of distal to aortic valve flow, mean velocity of distal to aortic valve flow, aortic root diameter, ascending aortic diameter, Iv end-diastolic volume: apical 2-chamber; modified ellipsoid, Iv end-diastolic volume: apical 4-chamber; modified ellipsoid, Iv end-diastolic volume: apical 2-chamber; single plane, Iv end-diastolic volume: apical 4-chamber; single plane, Iv end-systolic volume: apical 2-chamber; modified ellipsoid, Iv end-systolic volume: apical 4-chamber; modified ellipsoid, Iv end-systolic volume: apical 2-chamber; single plane, Iv end-systolic volume: apical 4-chamber; single plane, iv septum dimension at end-diastole, left atrium dimension, left atrium volume derived from apical 2-chamber; modified ellipsoid, left atrium volume derived from apical 4-chamber; modified ellipsoid, velocity-time integral proximal to the obstruction, maximum Iv velocity proximal to the obstruction, mean Iv velocity proximal to the obstruction, Iv area at end-diastole derived from apical 2-chamber, Iv area at end-diastole derived from apical 4-chamber, Iv area at end-systole derived from apical 2-chamber, Iv area at end-systole derived from apical 4-chamber, Iv internal dimension at end-diastole, Iv internal dimension at end-systole, Iv long-axis length at end-diastole derived from apical 2-chamber, Iv long-axis length at end-diastole derived from apical 4-, chamber, Iv long-axis length at end systole derived from apical 2-, chamber, Iv long-axis length at end systole derived from apical 4-chamber, Iv outflow tract area, Iv outflow tract diameter, Iv posterior wall thickness at end-diastole, mitral regurgitation maximum velocity, a-point maximum velocity of mitral flow, e-point maximum velocity of mitral flow, maximum velocity of mitral valve flow, mitral valve deceleration slope, mitral valve deceleration time, maximum velocity of distal to pulmonic valve flow, pulmonary artery acceleration slope, pulmonary artery acceleration time, pulmonary r-r time interval, right atrial end-systolic mean pressure, right ventricle dimension at end-diastole, tricuspid regurgitation maximum velocity, aortic valve regurgitation, mitral valve regurgitation, tricuspid valve regurgitation, pulmonary valve regurgitation, aortic valve stenosis, mitral valve stenosis, tricuspid valve stenosis, pulmonary valve stenosis, and physician-reported diastolic function. The diagnosis parameters can include diagnosis of acute rheumatic fever, diagnosis of chronic rheumatic heart disease, diagnosis of hypertensive diseases, diagnosis of ischemic heart diseases, diagnosis of pulmonary heart disease and diseases of pulmonary circulation, diagnosis of acute pericarditis, diagnosis of other forms of heart disease, diagnosis of acute myocarditis, diagnosis of cardiomyopathy, diagnosis of cardiac arrest, diagnosis of paroxysmal tachycardia, diagnosis of atrial fibrillation, diagnosis of heart failure, diagnosis of cerebrovascular diseases, diagnosis of diseases of arteries, arterioles and capillaries, diagnosis of diseases of veins, lymphatic vessels, and lymph nodes, diagnosis of hypotension, diagnosis of other and unspecified disorders of the circulatory system, diagnosis of diabetes mellitus, diagnosis of congenital heart defect, diagnosis of dyslipidemia, and diagnosis of chronic kidney disease.

In the method, the echocardiographic video of the heart associated with the patient can be associated with a single echocardiographic view. The single echocardiographic view can be a parasternal long axis view.

The method can further include generating a report based on the mortality risk score, the report including at least one of information about potential treatments for the patient or links to information about the potential treatments for the patient, the potential treatments for the patient including at least one of cardiac transplantation, implantation of mechanical support devices, defibrillator placement, palliative care, or hospice.

In the method, the mortality risk score associated with the patient can provide sufficient information to the medical practitioner or healthcare administrator for the medical practitioner or healthcare administrator to make a determination about a potential treatment for the patient, the potential treatment including at least one of cardiac transplantation, implantation of mechanical support devices, defibrillator placement, palliative care, or hospice. The determination can be eligibility for the treatment.

Some embodiments of the present disclosure provide a system. The system includes at least one processor coupled to at least one memory including instructions, the at least one processor executing the instructions to receive an echocardiographic video of a heart associated with a patient, provide the echocardiographic video to a trained neural network, the trained neural network being trained to generate a mortality risk score based on input echocardiographic video, receive a mortality risk score associated with the patient from the trained neural network, and output the mortality risk score associated with the patient to at least one of a memory or a display for viewing by a medical practitioner or healthcare administrator.

In the system, the at least one processor can further execute the instructions to receive electronic health record information associated with the patient, and provide the electronic health record information to the trained neural network, the trained neural network being further trained to generate the mortality risk score based on input electronic health record information, the electronic health record information including values of a number of parameters including age, tricuspid regurgitation maximum velocity, heart rate, low density lipoprotein, left ventricular ejection fraction, diastolic pressure, pulmonary artery acceleration time, systolic pressure, pulmonary artery acceleration slope, and diastolic function.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

Figure 1:
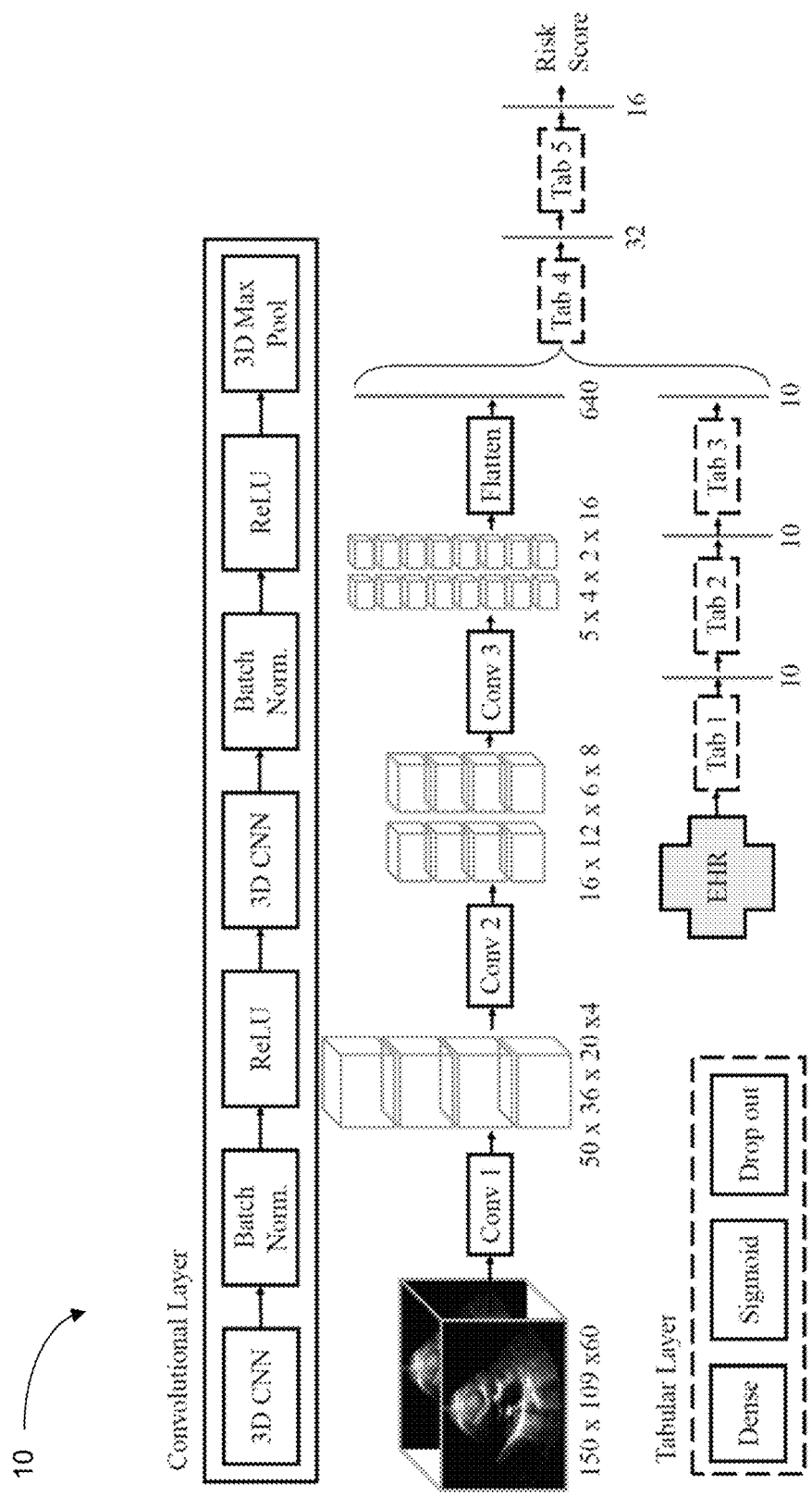
FIG. 1 is a neural network architecture for mortality prediction from echocardiography videos and electronic health record (EHR) data.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE DISCLOSURE

The various aspects of the subject invention are now described with reference to the annexed drawings. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (such as hard disk, floppy disk, magnetic strips), optical disks (such as compact disk (CD), digital versatile disk (DVD)), smart cards, and flash memory devices (such as card, stick). Additionally it should be appreciated that a carrier wave can be employed to carry computer-readable electronic data such as those used in transmitting and receiving electronic mail or in accessing a network such as the Internet or a local area network (LAN). Transitory computer-readable media (carrier wave and signal based) should be considered separately from non-transitory computer-readable media such as those described above. Of course, those skilled in the art will recognize many modifications may be made to this configuration without departing from the scope or spirit of the claimed subject matter.

Hereafter, unless indicated otherwise, the following terms and phrases will be used in this disclosure as described. The term "provider" will be used to refer to an entity that operates the overall system disclosed herein and, in most cases, will include a company or other entity that runs servers and maintains databases and that employs people with many different skill sets required to construct, maintain and adapt the disclosed system to accommodate new data types, new medical and treatment insights, and other needs. Exemplary provider employees may include researchers, clinical trial designers, oncologists, neurologists, psychiatrists, data scientists, and many other persons with specialized skill sets.

The term "physician" will be used to refer generally to any health care provider including but not limited to a primary care physician, a medical specialist, an oncologist, a neurologist, a nurse, and a medical assistant, among others.

The term "researcher" will be used to refer generally to any person that performs research including but not limited to a radiologist, a data scientist, or other health care provider. One person may be both a physician and a researcher while others may simply operate in one of those capacities.

Recent advances in "deep" learning (deep neural network; DNN) technologies; such as Convolutional Neural Networks (CNNs), Recurrent Neural Networks (RNN), Dropout Regularization, and adaptive gradient descent algorithms; in conjunction with massively parallel computational hardware (graphic processing units), have enabled state-of-the-art predictive models for image, time-series, and video-based data. For example, DNNs have shown promise in diagnostic applications, such as diabetic retinopathy, skin cancer, pulmonary nodules, cerebral microhemorrhage, and etiologies of cardiac hypertrophy. Yet, the opportunities with machine learning are not limited to such diagnostic tasks.

Prediction of future clinical events, for example, is a natural but relatively unexplored extension of machine learning in medicine. Nearly all medical decisions rely on accurate prediction. A diagnosis is provided to patients since it helps to establish the typical future clinical course of patients with similar symptoms, and a treatment is provided as a prediction of how to positively impact that predicted future clinical course. Thus, using computer-based methods to directly predict future clinical events is an important task where computers can likely assist human interpretation due to the inherent complexity of this problem. For example, a recent article in 216,221 patients demonstrated how a Random Forest model can predict in-hospital mortality with high accuracy. Deep learning models have also recently been used to predict mortality risk among hospitalized patients to assist with palliative care referrals. In cardiology, variables derived from electronic health records have been used to predict two-to-five year all-cause mortality in patients undergoing coronary computed tomography, five-year cardiovascular mortality in a general clinical population, and up to five-year all-cause mortality in patients undergoing echocardiography.

Notably, these initial outcome prediction studies in cardiology exclusively used human-derived, i.e. "hand-crafted" features from imaging, as opposed to automatically analyzing the raw image data. While this use of hand-crafted features is important, an approach that is unbiased by human opinions and not limited by human perception, human ability in pattern recognition, and effort may be more robust. That is, there is strong potential in an automated analysis that would leverage all available data in the images rather than a few selected clinical or clinically inspired measurements. Furthermore, the potential benefit of this approach for echocardiography may be enhanced by the added availability of rich temporal (video) data. DNNs make this unique approach possible. However, using video data also increases technical complexity and thus initial efforts to apply deep learning to echocardiography have focused on ingesting individual images rather than full videos.

In this disclosure, it is shown that a DNN can predict 1-year mortality directly from echocardiographic videos with good accuracy and that this accuracy can be improved by incorporating additional clinical variables from the electronic health record. This is done through a technical advance that leverages the full echocardiographic videos to make predictions using a three-dimensional DNN. In addition to this technical advance, direct clinical relevance is demonstrated by showing that the DNN is more accurate in predicting 1-year mortality compared to two expert physician cardiologists.

Results

A fully 3D Convolutional Neural Network (CNN) design is utilized in this study (FIG. 1). CNNs are neural networks that exploit spatial coherence in an image to significantly reduce the number of parameters that a fully connected network would need to learn. CNNs have shown promise in image classification tasks, even surpassing human abilities. Details of additional model architectures attempted (including a time-distributed 2D CNN+long short term memory network [LSTM]) are described in the methods.

FIG. 1 is a neural network architecture 10 for mortality prediction from echocardiography videos and electronic health record (EHR) data. The convolutional layer (Cony) is shown in the top box with a solid outline and the tabular EHR data layer (Tab) is shown in the bottom box with a dashed outline. The convolutional layer consists of Convolutional Neural Networks (CNN), Batch Normalizations (Batch Norm.), rectified linear units (ReLU), and a three-dimensional Maximum Pooling layer (3D Max Pool). The tabular layer consists of a fully connected layer (Dense) with sigmoid activations and a Drop Out layer. The input video dimensions were 150×109×60 pixels, and the output dimension of every layer are shown. The mortality prediction is output as a risk score that is associated with a predicted mortality of a patient.

Figure 2:
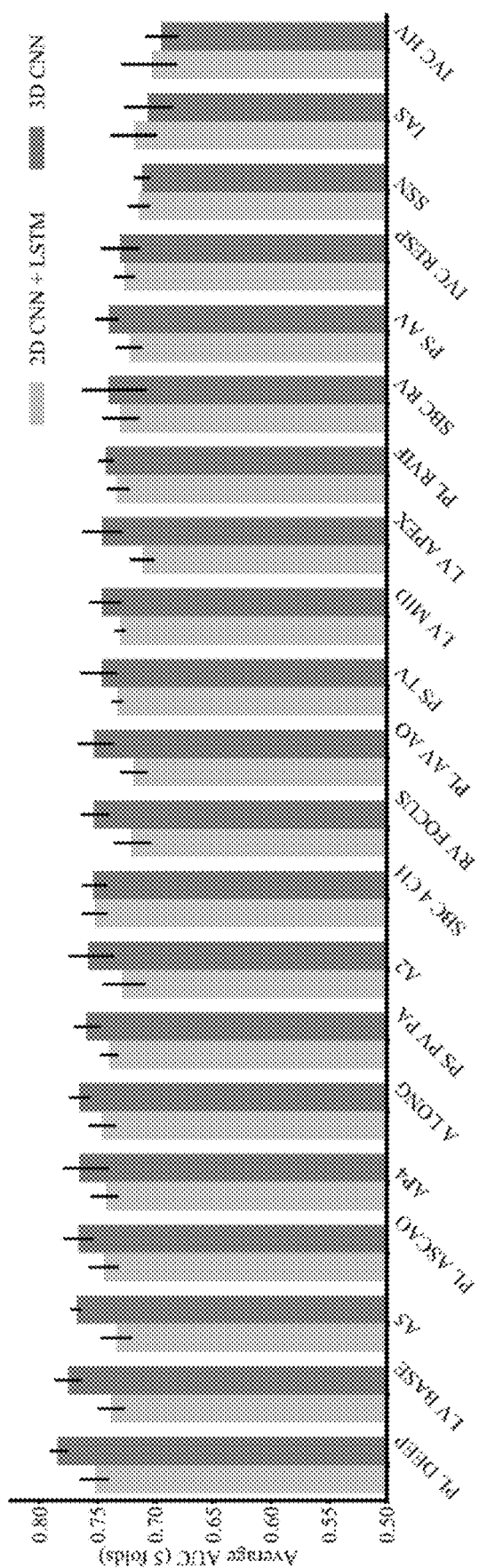
FIG. 2 is a one-year mortality prediction performance ranking for echocardiography views alone.

723,754 clinically acquired echocardiographic videos were acquired (approximately 45 million images) from 27,028 patients that were linked to at least 1 year of longitudinal follow-up data to know whether the patient was alive or dead within that time frame. Overall, 16% of patients in this cohort were deceased within a year after the echocardiogram was acquired. Based on a power calculation dardized according to clinical guidelines. Separate models were generated for each of the 21 standard echocardiographic views and showed that the proposed models were able to accurately predict 1-year survival using only the raw video data as inputs (FIG. 2). The chosen 3D CNN architecture (AUC range: 0.695-0.784) outperformed the 2D CNN+LSTM architecture (AUC range: 0.703-0.752) for most views. In both cases, the parasternal long-axis ("PL DEEP") view had the best performance. This result was in line with clinical intuition, since the PL DEEP view is typically reported by cardiologists as the most informative "summary" view of overall cardiac health. This is because the PL DEEP view contains elements of the left ventricle, left atrium, right ventricle, aortic and mitral valves, and whether or not there is a pericardial or left pleural effusion all within a single view.

FIG. 2 is a one-year mortality prediction performance ranking for each echocardiography view alone (no EHR data) using the 2D CNN+LSTM architecture (gray) and 3D CNN (blue) models. The error bars denote one standard deviation above and below the average across 5 folds. See Table 1 below for all view label abbreviations.

TABLE 1

| VIEW TYPE | VIEW TAG |
|---|---|
| APICAL 2 | a2, ap2 2d, a2 2d, a2 lavol, la 2ch |
| APICAL 3 | a long, ap3 2d, a3 2d |
| APICAL 4 | ap4, ap4 2d, a4 2d, a4 zoom, a4 lavol, la ap4 ch |
| APICAL 4 FOCUSED TO RV | rv focus, rvfocus |
| APICAL 5 | a5, ap5 2d, a5 2d |
| PARASTERNAL LONG AXIS | pl deep, psl deep |
| PARASTERNAL LONG ASCENDING AORTA | pl ascao, asc ao, pl asc ao |
| PARASTERNAL LONG MITRAL VALVE | pla mv |
| PARASTERNAL LONG PULMONIC VALVE | pl pv, pv lax |
| PARASTERNAL LONG RV INFLOW | pl rvif, rv inf, rvif 2d |
| PARASTERNAL LONG ZOOM AORTIC VALVE | pl av ao, av zoom |
| PARASTERNAL SHORT AORTIC VALVE | ps av, psavzoom, psax av |
| PARASTERNAL SHORT PULMONIC VALVE AND PULMONARY ARTERY | ps pv pa, ps pv, psax pv |
| PARASTERNAL SHORT TRICUSPID VALVE | ps tv, ps tv 2d, psax tv |
| SHORT AXIS APEX | sax apex |
| SHORT AXIS BASE | lv base |
| SHORT AXIS MID PAPILLARY | sax mid, sax |
| SUBCOSTAL 4CHAMBER | sbc 4 ch, sbc 4, sbc 4ch |
| SUBCOSTAL HEPATIC VEIN | ivc hv, sbc hv |
| SUBCOSTAL INTER-ATRIAL SEPTUM | ias, sbc ias, ias 2d |
| SUBCOSTAL IVC WITH RESPIRATION | ivc resp, sbc ivc, ivc insp, ivc snif, ivcsniff, sniff |
| SUBCOSTAL RV | sbc rv |
| SUPRASTERNAL NOTCH | ssn, ssn sax |
| PARASTERNAL LONG LAX | lax |
| SHORT AXIS MID PAPILLARY | lv mid |
| SHORT AXIS APEX | lv apex |
| APICAL 3 ZOOM | ap3 |
| APICAL 2 ZOOM | ap2 |
| SHORT AXIS BASE | sax base | detailed in the methods, data was separated from 600 patients for validation and comparison against two independent cardiologists and the remaining data was used for 5-fold cross-validation schemes.

During the acquisition of an echocardiogram (or any other medical video acquisition of the heart including but not limited to videos generated using cardiac MRI or CT), images of the heart and large blood vessels are acquired in different two-dimensional planes, or "views", that are standardized according to clinical guidelines.

Figure 4:
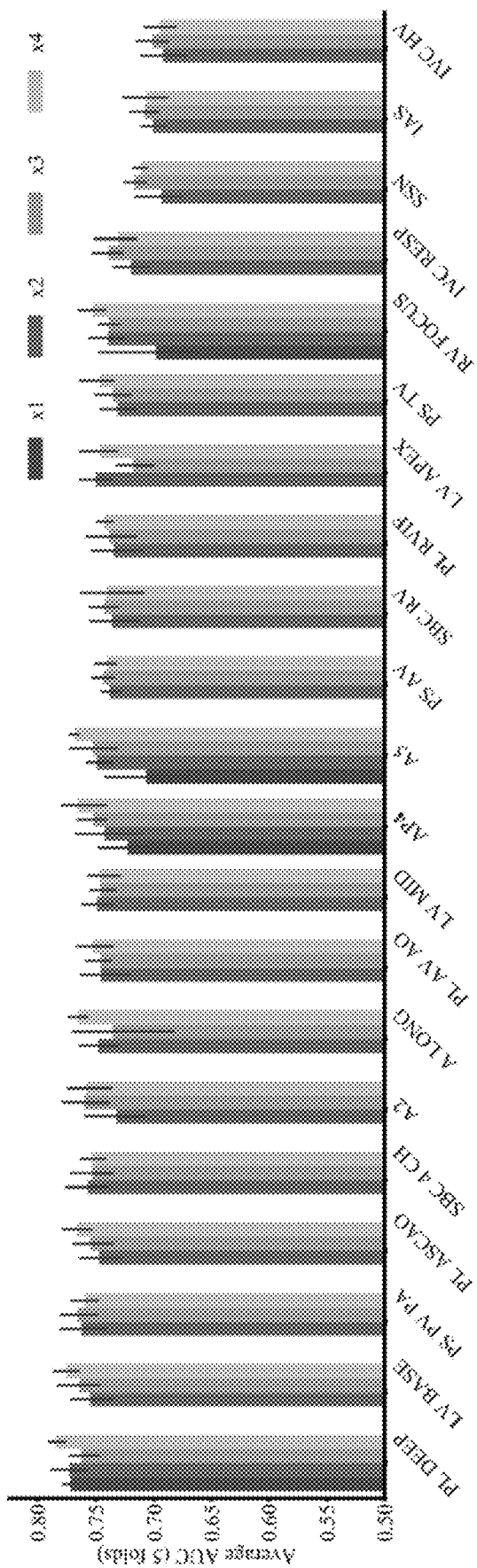
FIG. 4 is a graph of AUCs of one-year mortality predictions across all views with different levels of reduced resolution ranging from native (×1) to 4-fold (×4).
Figure 10:
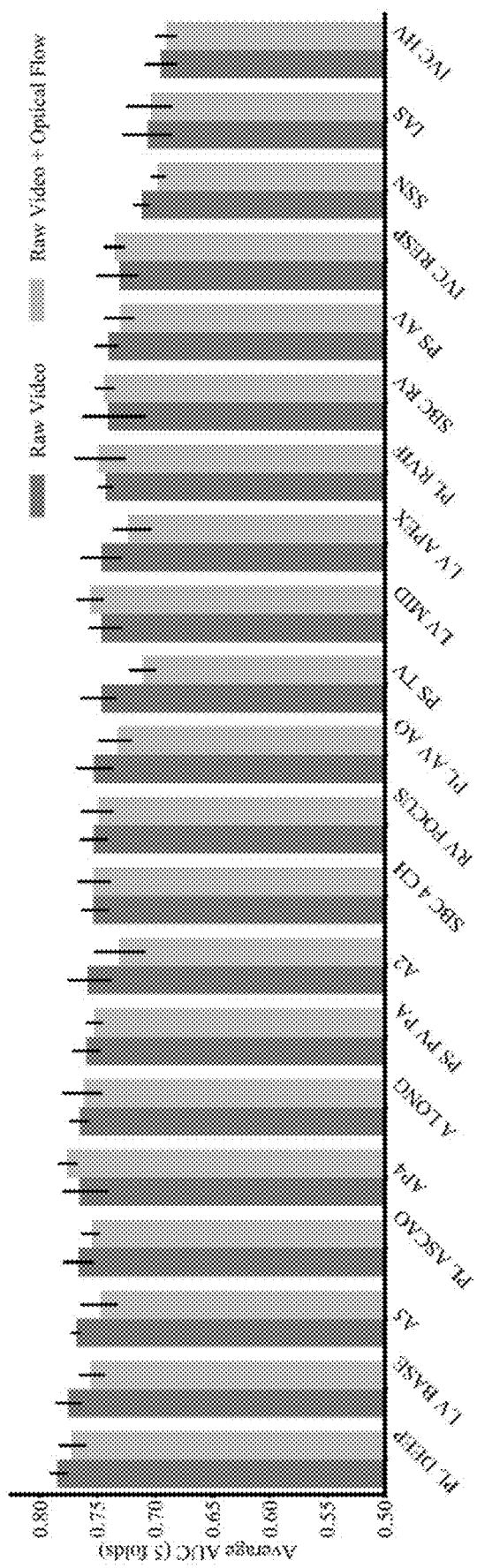
FIG. 10 is a graph of one-year mortality prediction performance ranking for all echocardiography views using only the raw video (blue) versus the raw video with optical flow features (gray).

These results were relatively insensitive to image resolution (no significant difference was observed between models using full native resolution images (400×600 pixels) and reduced resolution images (100×150 pixels); FIG. 4). FIG. 4 is a graph of AUCs of one-year mortality predictions across all views with different levels of reduced resolution ranging from native (×1) to 4-fold (×4). Similarly, adding derived optical flow velocity maps to the models along with the pixel level data did not improve prediction accuracy (FIG. 10). FIG. 10 is a graph of one-year mortality prediction performance ranking for all echocardiography views using only the raw video (blue) versus the raw video with optical flow features (gray). Note that full native resolution training was only done for select views due to the computational time required to complete the experiment at this resolution.

Next, the predictive accuracy of the models was investigated at additional survival intervals, including 3, 6, 9, and 12-month intervals after echocardiography. The models generally performed better at longer intervals, but AUCs for all cases were greater than 0.64 (FIG. 5).

Figure 5:
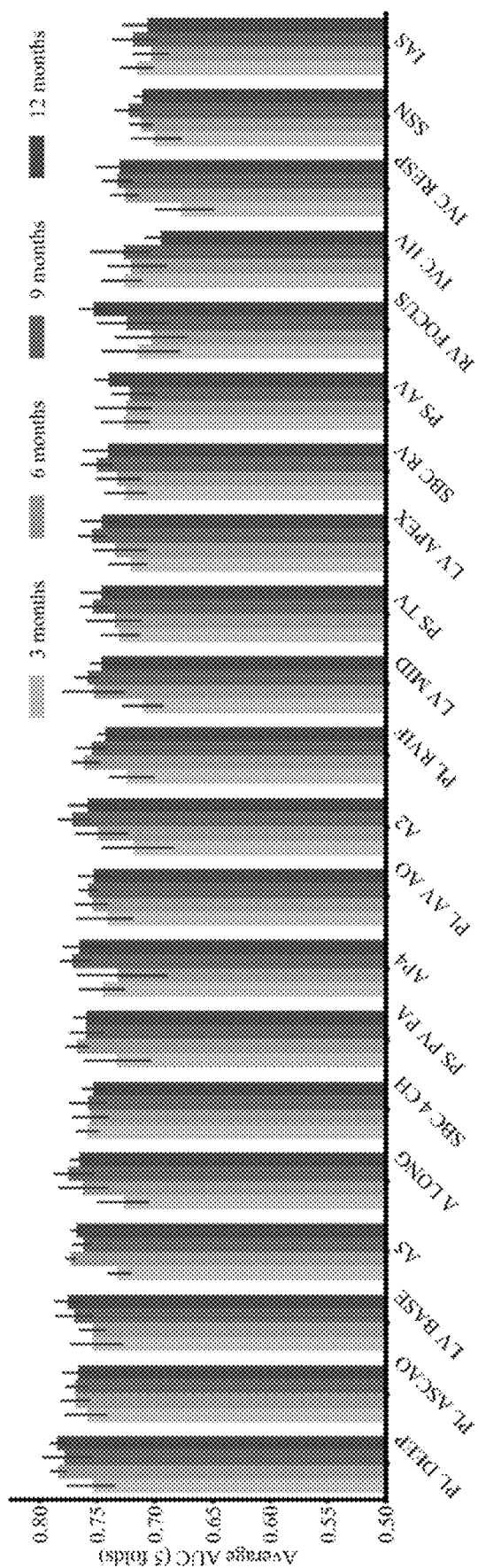
FIG. 5 is a graph of mortality prediction performance for echocardiographic videos alone at 3, 6, 9 and 12 months for all views.

FIG. 5 is a graph of mortality prediction performance for echocardiographic videos alone at 3, 6, 9 and 12 months for all views. The error bars denote one standard deviation above and below the average across 5 folds.

Clinical ("EHR") variables are then selected from each patient including age, tricuspid regurgitation maximum velocity, heart rate, low density lipoprotein [LDL], left ventricular ejection fraction, diastolic pressure, pulmonary artery acceleration time, systolic pressure, pulmonary artery acceleration slope, and diastolic function. These ten variables have previously been shown to contain >95% of the power for predicting 1-year survival in 171,510 patients and their addition improved accuracy to predict 1-year survival for all echocardiographic views, with AUCs ranging from 0.79-0.82 (compared to 0.70-0.78 without these ten EHR variables). Next, a software platform was developed (see "Methods" below) that was used to display an echocardiographic video of interest along with the 10 select EHR variables to two independent cardiologist echocardiographers who were blinded to the clinical outcomes. The cardiologists assessed whether each of 600 patients (independent test set extracted randomly from the original dataset of parasternal long axis views and not used for training of the machine) would be alive at one year based on the data presented. The final trained model (trained in all but these 600) was also applied to the same independent test set.

Figure 6B:
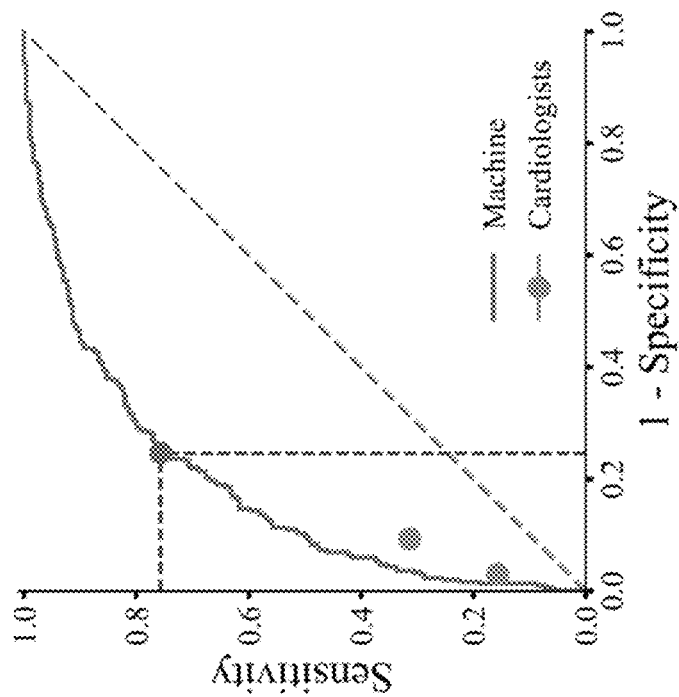
FIG. 6B is a receiver operating characteristic curve for the two cardiologists and the machine which demonstrates prediction performance.
Figure 6A:
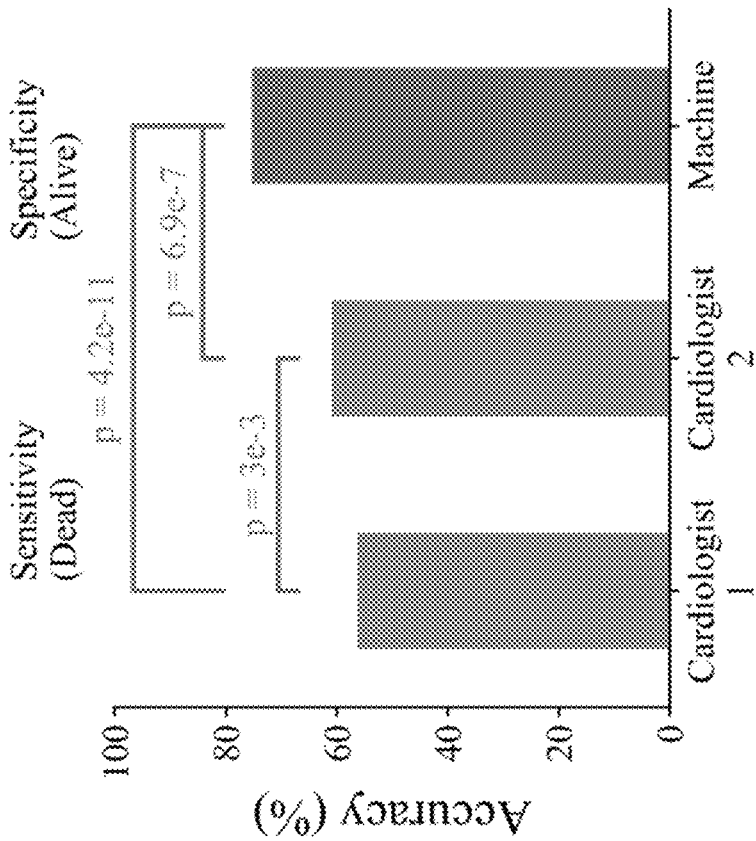
FIG. 6A is a graph of accuracy percentage for two cardiologists compared to a machine.

The overall accuracy of the model (75%) was significantly higher than that of the cardiologists (56% and 61%, $p=4.2\times10^{-11}$ and $6.9\times10^{-7}$ by Bonferroni-adjusted post-hoc analysis, FIG. 6A. The cardiologists were found to tend to overestimate survival likelihood, yielding high specificities (97% and 91%, respectively) but poor sensitivities (16% and 31%, respectively) while the model, by design, balanced sensitivity and specificity (both 75%). Moreover, as demonstrated in FIG. 6B, the operating points for the individual cardiologists fell below the model's receiver operating characteristic curve (as opposed to falling at a different point on the same curve), suggesting inferior predictive performance in this task.

FIGS. 6A and 6B are graphs of cardiologists vs Machine performance for 1-year mortality prediction from the survey dataset of 600 samples with balanced prevalence. FIG. 6A shows accuracy percentage of each cardiologist and the machine, and FIG. 6B shows sensitivity vs. specificity for each cardiologist and the machine. FIG. 6A shows the accuracy in bars and sensitivity (red) and specificity (green) as triangles. FIG. 6B shows the operating points of the cardiologists as orange dots, the Receiver Operating Characteristic curve for the machine performance in blue, and the machine operating point as a blue dot.

Beyond the limited inputs selected for the clinical expert comparison, the inventors sought to further characterize the model performance unconstrained by data input limitations. That is, additional experiments permuting the input combinations of structured data (none, limited set [top ten EHR variables], full set [158 EHR variables, as described in "Methods" below]) and echocardiography videos (none, single view, all 21 views) were completed. Models without videos were trained using all available data in the structured echocardiography measurement database (501,449 valid studies), while the models with videos were trained with all videos available for each view, ranging from 11,020 to 22,407 for single videos and 26,428 combined. In all cases, the test set was the 600 patients held out for the clinical expert comparison.

Table 2 below shows that all videos combined with the full EHR variable set had the highest AUC in the held out test set of 600 studies, demonstrating the potential to further enhance the performance of the already clinically superior model. Several general trends were also noted. First, a single video view out-performed a model that included 10 EHR variables as input. Second, multiple videos had higher performance than single videos. Third, the learning curves (FIG. 7) for multi-video predictions demonstrated that, despite having access to a massive dataset (26,428 echocardiographic videos), more samples would likely result in even higher performance for multi-video predictions. In contrast, the performance of the full EHR data-only model, which was consistently less than the full EHR plus videos model, was beginning to plateau. Hence, the novel multi-modal DNN approach, inclusive of echocardiography videos, provides enhanced performance for this clinical prediction task compared to what can be achieved using EHR data alone (inclusive of hand-crafted features derived by humans from the videos).

TABLE 2

|  | NO VIDEO (~500K SAMPLES) | SINGLE VIDEO (~22K SAMPLES) | ALL VIDEOS (~27K SAMPLES) |
| --- | --- | --- | --- |
| NO EHR VARIABLES | 0.532 | 0.801 | 0.839 |
| LIMITED EHR SET | 0.786 | 0.824 | 0.843 |
| FULL EHR SET | 0.851 | 0.825 | 0.858 |

Table 2 shows AUC scores for each data modality combination of EHR and Echo video data on the 600 left out studies used to compare to the cardiologists. "No video" models were trained on all available studies, whereas "Single Video" and "All Videos" were trained on a subset where video data were available. The No EHR variables and No Video cell denotes a random guess.

Figure 7:
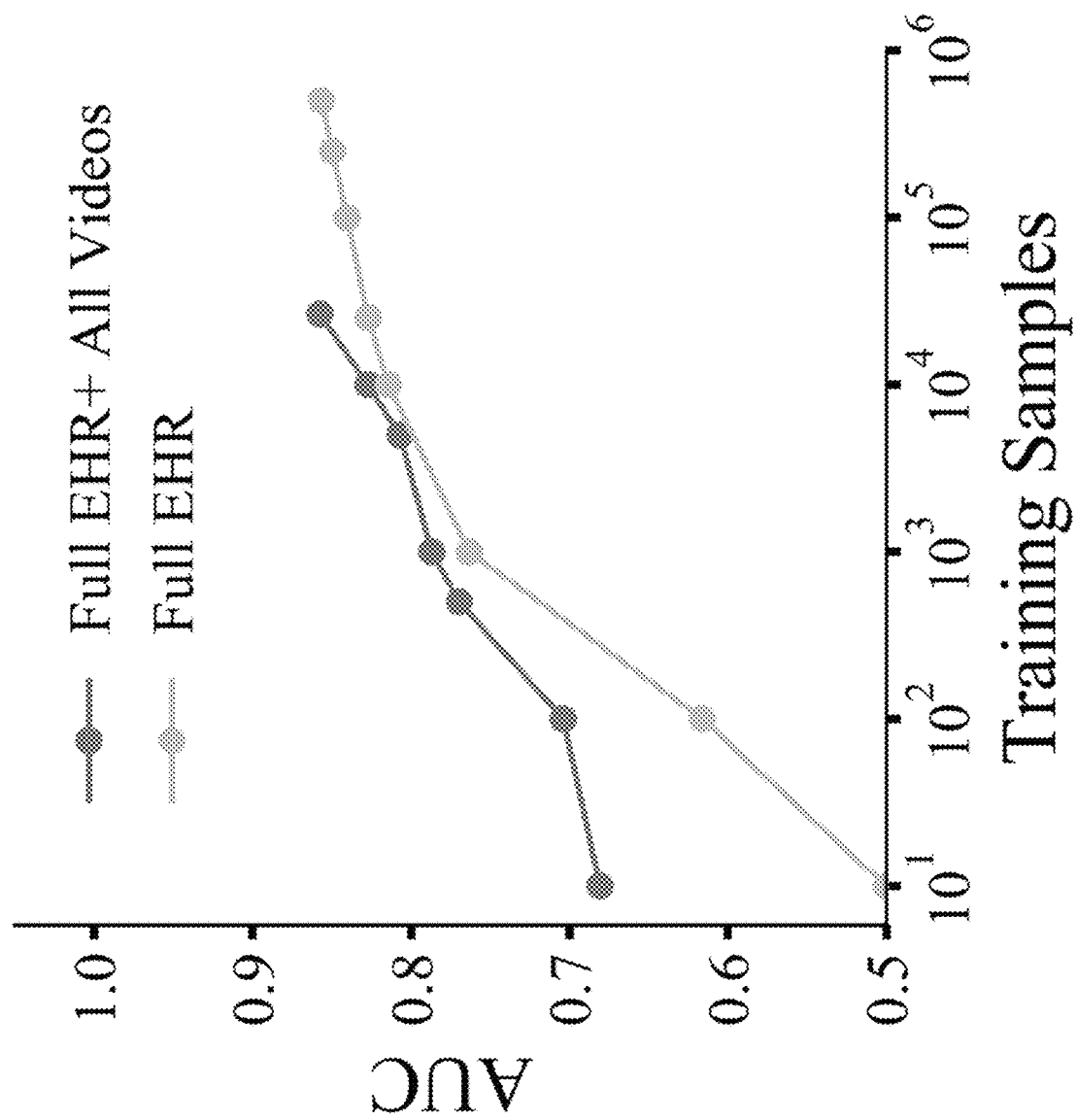
FIG. 7 is a graph of learning curves for a full (one hundred and fifty-eight) EHR variables model compared to the full EHR variables plus videos model.

FIG. 7 is a graph of learning curves for the full (158) EHR variables model compared to the full EHR variables plus videos. The AUC is reported on the 600 patient set as a function of training set size, ranging from 10 to the maximum number of datasets available for the given data inputs, which was 501,449 for the EHR variables and 26,428 for the Full EHR+videos.

The potential for DNNs to help cardiologists predict a clinically relevant endpoint, for example mortality after echocardiography, using both raw video data and relevant clinical data extracted from the electronic health record, is demonstrated. For training the DNN, a dataset of 723,754 clinically-acquired videos of the heart consisting of ~45 million images was leveraged. The ability of the DNN to discriminate 1-year survival—even with limited model inputs—was shown to surpass that of trained cardiologists, suggesting that these models can add value beyond a standard clinical interpretation. To the knowledge of the inventors, no prior study has demonstrated the ability to train a deep neural network to predict a future clinically-relevant event directly from image pixel-level data. Additional experiments demonstrated opportunities to achieve further significant performance gains by incorporating more EHR variables, simultaneously using all echocardiography views, and leveraging more data for model training.

1-year all-cause mortality was chosen as a highly important, easily measured clinical outcome to demonstrate feasibility for this initial work. Importantly, all-cause mortality is a well-defined endpoint without the bias that can be introduced into endpoints such as cardiovascular-specific mortality, and it can easily be extracted from an EHR that is validated against national death index databases. Moreover, mortality prediction is highly relevant for numerous applications in cardiology, as evidenced by the multitude of clinical risk scores that are currently used clinically (Framingham, TIMI, and GRACE scores, etc.). It is understood that a DNN may be trained to predict all-cause mortality over time periods other than one year, for example, six months, two years, three years, five years, etc. Moreover, a DNN may be trained to predict many other clinically relevant endpoints such as hospitalization, onset of future disease, response to a treatment, healthcare utilization, etc.

Methods

Image Collection and Preprocessing

An echocardiography study consists of several videos containing multiple views of the heart. Two clinical databases, Philips iSite and Xcelera, contained all echocardiograms collected at Geisinger. DCM4CHEE (version 2.0.29) and AcuoMed (version 6.0) software were used to retrieve a DICOM file for each echocardiography video.

Figure 8B:
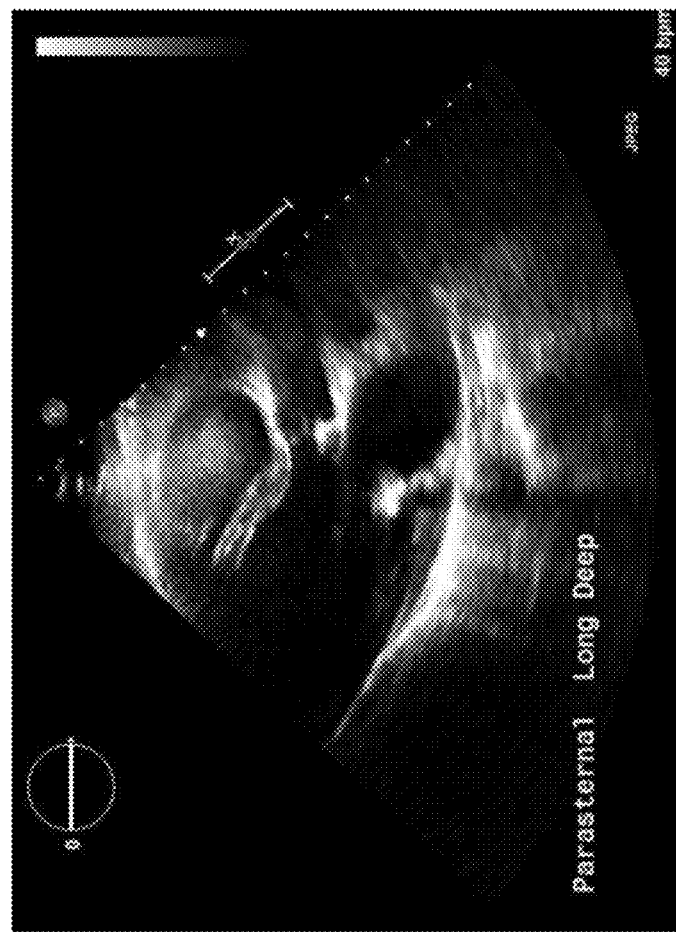
FIG. 8B is an exemplary annotated video.
Figure 8A:
FIG. 8A is an exemplary raw video.

The retrieved DICOM files contained an annotated video (for example, which was marked with the view name) and a raw video when the equipment was configured to store it. Without loss of generality, raw videos were used for all analyses. FIG. 8A is an exemplary raw video, and FIG. 8B is an exemplary annotated video. The raw video contained only the beam-formed ultrasound image stored in a stream of bytes format, whereas the annotated video contained artificial annotations on top of the raw video. All raw videos were linearly interpolated to 30 frames per second.

Along with the video data, the DICOM file included tags that labelled the view as to which specific image orientation was acquired. These view tags had slight variations across studies for the same type of view. For example, an apical four chamber view could be tagged as "a4", "a4 2d", or "ap4". Samples of each unique tag were visually inspected and grouped them into 30 common views (Table 1). Since each video from a view group could potentially have different dimensions, all videos were normalized from a view to the most common row and column dimensions. Each frame was cropped/padded with zeros to match the most common dimensions among the view group. Ultimately, Philips-generated DICOM files with raw videos and view labels were retrieved and any videos that lasted less than 1 second were excluded.

Electronic Health Record Data Preprocessing

The EHR contained 594,862 echocardiogram studies from 272,280 unique patients performed over 19 years (February 1998 to September 2018). For each study, automatic and physician reported echocardiography measurements (n=480) were extracted along with patient demographic (n=3), vitals (n=5), laboratory (n=2), and problem list diagnostic codes (n=90; International Classification of Diseases, Tenth Revision (ICD-10)). For measurements taken outside of the Echocardiography study, such as fasting LDL, HDL, blood pressure, heart rate, and weight and height measurements, the closest (before or after) within a six-month window was retrieved.

All continuous variables were cleaned from physiologically out of limit values, which may have been caused by input errors. In cases where no limits could be defined for a measurement, extreme outliers were removed that met two rules: 1) Value beyond the mean plus or minus three standard deviations and 2) Value below the $25^{th}$ percentile minus 3 interquartile ranges or above the $75^{th}$ percentile plus 3 interquartile ranges. The removed outlier values were set as missing.

The missing data was imputed from continuous variables in two steps. First, a time interpolation was conducted to fill in missing measurements using all available studies of an individual patient, i.e., missing values in between echocardiography sessions were linearly interpolated if complete values were found in the adjacent echocardiograms. Then, to conduct Multiple Imputation by Chained Equations (MICE) and complete the entire dataset, 115 of 480 echocardiography measurement variables with more than 10% non-missing measurements were kept.

The reported diastolic function was coded in an ordinal fashion with −1 for normal, 0 for dysfunction (but no grade reported), and 1, 2 and 3 for diastolic dysfunction grades I, II, and III respectively. After imputation of the continuous measurements, the missing diastolic function assessment was imputed by training a logistic regression classifier to predict the dysfunction grade (−1, 1, 2, or 3) in a One-vs-All classifier framework using 278,160 studies where diastolic function was known.

Following imputation, the physician reported left ventricular ejection fraction (LVEF) plus 57 other independent, non-redundant echocardiography measurements (i.e., excluding variables derived from other measurements were retained; n=58 echocardiography measurements in total).

The patient's age and survival time were calculated from the date of the echocardiogram. The patient status (dead/alive) was based on the last known living encounter or confirmed death date, which is cross-referenced against national death index databases monthly in the EHR from which it was retrieved.

A list and description of all 158 EHR variables used in the proposed models is presented in Table 3 below.

TABLE 3

| | EHR VARIABLE | UNITS | VARIABLE CLASS | DESCRIPTION |
|---|---|---|---|---|
| 1 | Age[1] | years | demographics | At the time of Echocardiography study |
| 2 | Sex | 0: Female, 1: Male | demographics | |
| 3 | Smoking status | 0: No, 1: Yes | demographics | Ever smoked |
| 4 | Height | cm | vitals | |

TABLE 3-continued

| | EHR VARIABLE | UNITS | VARIABLE CLASS | DESCRIPTION |
|---|---|---|---|---|
| 5 | Weight | kg | vitals | |
| 6 | Heart rate | bpm | vitals | |
| 7 | Diastolic blood pressure | mm Hg | vitals | |
| 8 | Systolic blood pressure | mm Hg | vitals | |
| 9 | LDL | mg/DL | laboratory | Low-density lipoprotein |
| 10 | HDL | mg/DL | laboratory | High-density lipoprotein |
| 11 | LVEF | % | Echo measure | Physician-reported left ventricular ejection fraction |
| 12 | AI dec slope | cm/s2 | Echo measure | Aortic insufficiency deceleration slope |
| 13 | AI max vel | cm/s | Echo measure | Aortic insufficiency maximum velocity |
| 14 | Ao V2 VTI | cm | Echo measure | Velocity-time integral of distal to aortic valve flow |
| 15 | Ao V2 max | cm/s | Echo measure | Maximum velocity of distal to aortic valve flow |
| 16 | Ao V2 mean | cm/s | Echo measure | Mean velocity of distal to aortic valve flow |
| 17 | Ao root diam | cm | Echo measure | Aortic root diameter |
| 18 | Asc Aorta | cm | Echo measure | Ascending aortic diameter |
| 19 | EDV MOD*-sp2 | ml | Echo measure | LV end-diastolic volume: apical 2-chamber, modified ellipsoid |
| 20 | EDV MOD*-sp4 | ml | Echo measure | LV end-diastolic volume: apical 4-chamber, modified ellipsoid |
| 21 | EDV sp2-el** | ml | Echo measure | LV end-diastolic volume: apical 2-chamber, single plane |
| 22 | EDV sp4-el** | ml | Echo measure | LV end-diastolic volume: apical 4-chamber, single plane |
| 23 | ESV MOD*-sp2 | ml | Echo measure | LV end-systolic volume: apical 2-chamber, modified ellipsoid |
| 24 | ESV MOD*-sp4 | ml | Echo measure | LV end-systolic volume: apical 4-chamber, modified ellipsoid |
| 25 | ESV sp2-el** | ml | Echo measure | LV end-systolic volume: apical 2-chamber, single plane |
| 26 | ESV sp4-el** | ml | Echo measure | LV end-systolic volume: apical 4-chamber, single plane |
| 27 | IVSd | cm | Echo measure | IV septum dimension at end-diastole |
| 28 | LA dimension | cm | Echo measure | Left atrium dimension |
| 29 | LAV MOD*-sp2 | ml | Echo measure | Left atrium volume: apical 2-chamber, modified ellipsoid |
| 30 | LAV MOD*-sp4 | ml | Echo measure | Left atrium volume: apical 4-chamber, modified ellipsoid |
| 31 | LV V1 VTI | cm | Echo measure | Velocity-time integral: proximal to the obstruction |
| 32 | LV V1 max | cm/s | Echo measure | Maximum LV velocity: proximal to the obstruction |
| 33 | LV V1 mean | cm/s | Echo measure | Mean LV velocity proximal to the obstruction |
| 34 | LVAd ap2 | cm2 | Echo measure | LV area at end-diastole: apical 2-chamber |
| 35 | LVAd ap4 | cm2 | Echo measure | LV area at end-diastole: apical 4-chamber |
| 36 | LVAs ap2 | cm2 | Echo measure | LV area at end-systole: apical 2-chamber |
| 37 | LVAs ap4 | cm2 | Echo measure | LV area at end-systole: apical 4-chamber |
| 38 | LVIDd | cm | Echo measure | LV internal dimension at end-diastole |
| 39 | LVIDs | cm | Echo measure | LV internal dimension at end-systole |
| 40 | LVLd ap2 | cm | Echo measure | LV long-axis length at end-diastole: apical 2-chamber |
| 41 | LVLd ap4 | cm | Echo measure | LV long-axis length at end-diastole: apical 4-chamber |

TABLE 3-continued

| | EHR VARIABLE | UNITS | VARIABLE CLASS | DESCRIPTION |
|---|---|---|---|---|
| 42 | LVLs ap2 | cm | Echo measure | LV long-axis length at end systole: apical 2-chamber |
| 43 | LVLs ap4 | cm | Echo measure | LV long-axis length at end systole: apical 4-chamber |
| 44 | LVOT area M | cm2 | Echo measure | LV outflow tract area |
| 45 | LVOT diam | cm | Echo measure | LV outflow tract diameter |
| 46 | LVPWd | cm | Echo measure | LV posterior wall thickness at end-diastole |
| 47 | MR max vel | cm/s | Echo measure | Mitral regurgitation maximum velocity |
| 48 | MV A point | cm/s | Echo measure | A-point maximum velocity of mitral flow |
| 49 | MV E point | cm/s | Echo measure | E-point maximum velocity of mitral flow |
| 50 | MV P1/2t max-vel | cm/s | Echo measure | Maximum velocity of mitral valve flow |
| 51 | MV dec slope | cm/s2 | Echo measure | Mitral valve deceleration slope |
| 52 | MV dec time | s | Echo measure | Mitral valve deceleration time |
| 53 | PA V2 max | cm/s | Echo measure | Maximum velocity of distal to pulmonic valve flow |
| 54 | PA acc slope | cm/s2 | Echo measure | Pulmonary artery acceleration slope |
| 55 | PA acc time | s | Echo measure | Pulmonary artery acceleration time |
| 56 | Pulm. R-R | s | Echo measure | Pulmonary R-R time interval |
| 57 | RAP systole | mm-Hg | Echo measure | Right atrial end-systolic mean pressure |
| 58 | RVDd | cm | Echo measure | Right ventricle dimension at end-diastole |
| 59 | TR max vel | cm/s | Echo measure | Tricuspid regurgitation maximum velocity |
| 60 | AVR | 0/1 Hot encoded for severity levels 0, 1, 2, 3 | Echo measure | Aortic valve regurgitation |
| 61 | MVR | 0/1 Hot encoded for severity levels 0, 1, 2, 3 | Echo measure | Mitral valve regurgitation |
| 62 | TVR | 0/1 Hot encoded for severity levels 0, 1, 2, 3 | Echo measure | Tricuspid valve regurgitation |
| 63 | PVR | 0/1 Hot encoded for severity levels 0, 1, 2, 3 | Echo measure | Pulmonary valve regurgitation |
| 64 | AVS | 0/1 Hot encoded for severity levels 0, 1, 2, 3 | Echo measure | Aortic valve stenosis |
| 65 | MVS | 0/1 Hot encoded for severity levels 0, 1, 2, 3 | Echo measure | Mitral valve stenosis |
| 66 | TVS | 0/1 Hot encoded for severity levels 0, 1, 2, 3 | Echo measure | Tricuspid valve stenosis |
| 67 | PVS | 0/1 Hot encoded for severity levels 0, 1, 2, 3 | Echo measure | Pulmonary valve stenosis |
| 68 | Diastolic function10 | −1: Normal, 0: abnormal (no grade reported), [1, 2, 3]: grade I/II/II | Echo measure | Physician-reported diastolic function |
| 69-71 | I00, I01, I02 | | Diagnosis code | Acute rheumatic fever |

TABLE 3-continued

| EHR VARIABLE | UNITS | VARIABLE CLASS | DESCRIPTION |
|---|---|---|---|
| 72-76 I05, I06, I07, I08, I09 | | Diagnosis code | Chronic rheumatic heart disease |
| 77-82 I10, I11, I12, I13, I15, I16 | | Diagnosis code | Hypertensive diseases |
| 83-88 I20, I21, I22, I23, I24, I25 | | Diagnosis code | Ischemic heart diseases |
| 89-91 I26, I27, I28 | | Diagnosis code | Pulmonary heart disease and diseases of pulmonary circulation |
| 92 I30 | | Diagnosis code | Acute pericarditis |
| 93-106 I31, I32, I33, I34, I35, I36, I37, I38, I39, I43, I44, I45, I49, I51 | | Diagnosis code | Other forms of heart disease |
| 107 I40 | | Diagnosis code | Acute myocarditis |
| 108 I42 | | Diagnosis code | Cardiomyopathy |
| 109 I46 | | Diagnosis code | Cardiac arrest |
| 110 I47 | | Diagnosis code | Paroxysmal tachycardia |
| 111 I48 | | Diagnosis code | Atrial fibrillation |
| 112 I50 | | Diagnosis code | Heart failure |
| 113-121 I60, I61, I62, I63, I65, I66, I67, I68, I69 | | Diagnosis code | Cerebrovascular diseases |
| 122-131 I70, I71, I72, I73, I74, I75, I76, I77, I78, I79 | | Diagnosis code | Diseases of arteries, arterioles and capillaries |
| 131-140 I80, I81, I82, I83, I85, I86, I87, I88, I89 | | Diagnosis code | Diseases of veins, lymphatic vessels, and lymph nodes |
| 141 I95 | | Diagnosis code | Hypotension |
| 142-144 I96, I97, I99 | | Diagnosis code | Other and unspecified disorders of the circulatory system |
| 145-149 E08, E09, E10, E11, E13 | | Diagnosis code | Diabetes mellitus |
| 150-156 Q20, Q21, Q22, Q23, Q24, Q25, Q26 | | Diagnosis code | Congenital heart defect |
| 157 E78 | | Diagnosis code | Dyslipidemia |
| 158 N18 | | Diagnosis code | Chronic kidney disease |

Data Pruning

The image collection and preprocessing resulted in 723,754 videos from 31,874 studies performed on 27,028 patients (an average of 22.7 videos per study). The imaging and EHR data were linked and any imaging without EHR data was discarded. For a given survival experiment (3, 6, 9, and 12 months), studies without enough follow up were also removed. After that, a single study per patient was kept by randomly sampling one study per patient. This ensured that images from a single patient would not appear multiple times throughout training, validation, and testing groups.

Figure 9:
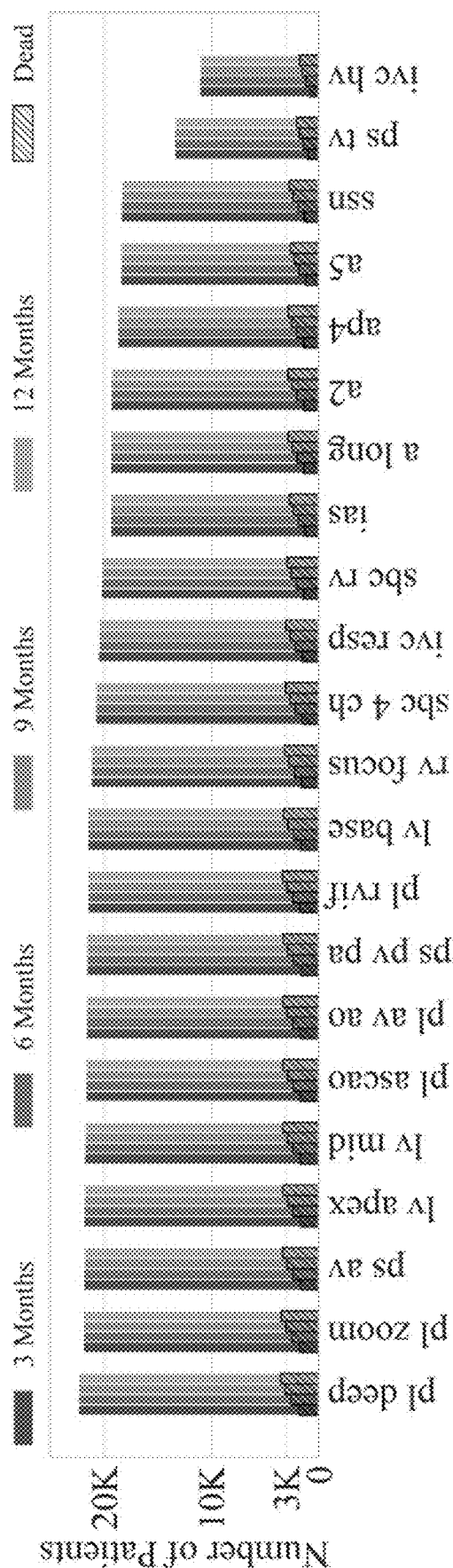
FIG. 9 is a plot of the number of patients for experiments that required 3, 6, 9, and 12 months follow-up.

At least 600 patients (300 alive, 300 deceased) were needed, as indicated by a sample size calculation using the Pearson Chi-square test, to estimate and compare prognostic accuracy between the model and the two cardiologists. A 10% difference in accuracy between machine and cardiologist (80% vs 70%), 80% power, a significance level of 5%, and an approximate 40% discordancy were assumed. This was calculated using Power Analysis Software (PASS v15). Thus, 300 studies of patients that survived and 300 that died within the set experiment threshold were randomly sampled for each view, and were set aside from the valid samples to later compare the performance of the machine against two independent cardiologists. Only the parasternal long axis view (representing the best performing model and the cardiologists' preference for the most comprehensive single view) was ultimately used for the cardiologist comparison. The total number of valid samples for each experiment and view is shown in Table 4 below, and FIG. 9. FIG. 9 is a plot of the number of patients for experiments that required 3, 6, 9, and 12 months follow-up (as indicated in Table 3 above) with the proportion of dead patients (shaded bar).

would be commonly found by the same 2D kernels across the video. This assumption was put in practice for echocardiography view classification. The LSTM layer aggregates the CNN features over time to output a vector that represents the entire sequence.

The 2D CNN+GAP approach exchanged the LSTM layers for the average CNN features as a time aggregation of frames. The GAP layer provides two advantages. It requires no trainable parameters, saving 1008 parameters from the LSTM layers, and enables feature interpretation. The final fully connected layer after the GAP would provide a weighted average of the CNN features, which could indicate what sections of the video weighted more in the final decision.

The 3D CNN approach aggregates time and space features as the input data flows through the network. 3D CNNs have also shown successful applications for video classification. As opposed to the 2D CNN approach, a 3D CNN

TABLE 4

| VIEW GROUP | 3 MONTHS | 6 MONTHS | 9 MONTHS | 12 MONTHS |
|---|---|---|---|---|
| APICAL 2 | 19,334 | 19,328 | 19,323 | 19,316 |
| APICAL 3 | 19,392 | 19,388 | 19,384 | 19,376 |
| APICAL 4 | 18,755 | 18,749 | 18,745 | 18,737 |
| APICAL 4 FOCUSED TO RV | 21,192 | 21,186 | 21,181 | 21,173 |
| APICAL 5 | 18,438 | 18,431 | 18,426 | 18,419 |
| PARASTERNAL LONG AXIS | 22,426 | 22,420 | 22,415 | 22,407 |
| PARASTERNAL LONG ASCENDING AORTA | 21,700 | 21,694 | 21,688 | 21,681 |
| PARASTERNAL LONG RV INFLOW | 21,544 | 21,538 | 21,534 | 21,528 |
| PARASTERNAL LONG ZOOM AORTIC VALVE | 21,657 | 21,650 | 21,645 | 21,637 |
| PARASTERNAL SHORT AORTIC VALVE | 21,875 | 21,870 | 21,865 | 21,857 |
| PARASTERNAL SHORT PULMONIC VALVE AND PULMONARY ARTERY | 21,614 | 21,609 | 21,605 | 21,596 |
| PARASTERNAL SHORT TRICUSPID VALVE | 13,385 | 13,379 | 13,375 | 13,370 |
| SHORT AXIS BASE | 21,541 | 21,535 | 21,530 | 21,523 |
| SUBCOSTAL 4 CHAMBER | 20,768 | 20,763 | 20,758 | 20,751 |
| SUBCOSTAL HEPATIC VEIN | 11,033 | 11,029 | 11,024 | 11,020 |
| SUBCOSTAL INTER-ATRIAL SEPTUM | 19,402 | 19,399 | 19,394 | 19,387 |
| SUBCOSTAL IVC WITH RESPIRATION | 20,510 | 20,505 | 20,499 | 20,492 |
| SUBCOSTAL RV | 20,263 | 20,259 | 20,254 | 20,247 |
| SUPRASTERNAL NOTCH | 18,382 | 18,378 | 18,372 | 18,365 |
| SHORT AXIS MID PAPILLARY | 21,801 | 21,796 | 21,791 | 21,783 |
| SHORT AXIS APEX | 21,870 | 21,864 | 21,859 | 21,851 |

Parasternal long mitral valve, parasternal long pulmonic valve, snort axis apex zoom, short axis mid papillary zoom, parasternal long lax, apical 3 zoom, and apical 2 zoom views were excluded, as they did not have enough available samples to run the experiments.

Model Selection

For Echocardiography video classification, four different architectures were explored: 1) A time-distributed two-dimensional Convolutional Neural Network (2D CNN) with Long Short-Term Memory (LSTM), 2) a time-distributed 2D CNN with Global Average Pooling (GAP), 3) a 3D CNN and 4) a 3D CNN with GAP. For simplicity, the four candidate architectures are abbreviated as follows: 2D CNN+LSTM, 2D CNN+GAP, 3D CNN, and 3D CNN+GAP.

The 2D CNN+LSTM consisted of a 2D CNN branch distributed to all frames of the video. This architecture was used for a video description problem, where all frames from a video belonged to the same scene or action. Since all frames of the echocardiography video belong to the same scene or view, it is correct to assume that the static features incorporates information from adjacent frames at every layer, extracting time-space dependent features.

The 3D CNN approach would replace the Flatten operation for a GAP layer. In a similar fashion to the 2D CNN+GAP approach, the GAP layer would reduce the number of input features to the final Dense layer, thus the reduction of the number of parameters from 641 to 17; while enabling the traceback of the contributions of video features.

The convolutional units of the 2D and 3D CNNs were defined as a sequence of 7 layers in the following composition: CNN layer, Batch Normalization, ReLU, CNN layer, Batch Normalization, ReLU, and Max Pooling (see FIG. 1). All kernel dimensions were set to 3 and Max Pooling was applied in a 3×3 window for 2D kernels and 3×3×3 for 3D kernels.

A detailed description of the number of parameters for the 2D CNN+LSTM architecture is shown in Table 5 below, 2D CNN+GAP is shown in Table 6 below, 3D CNN is shown in Table 7 below, and 3D CNN+GAP is shown in Table 8.

TABLE 5

| LAYER NAME | INPUT DIMENSIONS | NUMBER OF PARAMETERS |
|---|---|---|
| TIME-DISTRIBUTED 2D CONV 1 | 60 × 109 × 150 × 1 | 40 + 16 + 148 + 16 = 220 |
| TIME-DISTRIBUTED 2D CONV 2 | 60 × 36 × 50 × 4 | 296 + 32 + 584 + 32 = 944 |
| TIME-DISTRIBUTED 2D CONV 3 | 60 × 12 × 16 × 8 | 1,168 + 64 + 2,320 + 64 = 3,616 |
| TIME-DISTRIBUTED 2D CONV 4 | 60 × 4 × 5 × 16 | 2,320 + 64 + 2,320 + 64 = 4,768 |
| TIME-DISTRIBUTED FLATTEN | 60 × 1 × 1 × 16 | 0 |
| LSTM 1 | 60 × 16 | 800 |
| LSTM 2 | 60 × 8 | 208 |
| DENSE | 4 | 5 |
| Total | | 10,561 |

TABLE 6

| LAYER NAME | INPUT DIMENSIONS | NUMBER OF PARAMETERS |
|---|---|---|
| TIME-DISTRIBUTED 2D CONV 1 | 60 × 109 × 150 × 1 | 40 + 16 + 148 + 16 = 220 |
| TIME-DISTRIBUTED 2D CONV 2 | 60 × 36 × 50 × 4 | 296 + 32 + 584 + 32 = 944 |
| TIME-DISTRIBUTED 2D CONV 3 | 60 × 12 × 16 × 8 | 1,168 + 64 + 2,320 + 64 = 3,616 |
| TIME-DISTRIBUTED 2D CONV 4 | 60 × 4 × 5 × 16 | 2,320 + 64 + 2,320 + 64 = 4,768 |
| GLOBAL AVERAGE POOLING | 60 × 4 × 5 × 16 | 0 |
| DENSE | 16 | 17 |
| Total | | 9,565 |

TABLE 7

| LAYER NAME | FEATURE DIMENSIONS | NUMBER OF PARAMETERS |
|---|---|---|
| 3D CONV 1 | 60 × 109 × 150 × 1 | 112 + 16 + 436 + 16 = 580 |
| 3D CONV 2 | 20 × 36 × 50 × 4 | 872 + 32 + 1,736 + 32 = 2672 |
| 3D CONV 3 | 6 × 12 × 16 × 8 | 3,472 + 64 + 6,928 + 64 = 10,528 |
| GLOBAL AVERAGE POOLING | 6 × 12 × 16 × 16 | 0 |
| DENSE | 16 | 17 |
| Total | | 13,797 |

TABLE 8

| LAYER NAME | FEATURE DIMENSIONS | NUMBER OF PARAMETERS |
|---|---|---|
| 3D CONV 1 | 60 × 109 × 150 × 1 | 112 + 16 + 436 + 16 = 580 |
| 3D CONV 2 | 20 × 36 × 50 × 4 | 872 + 32 + 1,736 + 32 = 2672 |
| 3D CONV 3 | 6 × 12 × 16 × 8 | 3,472 + 64 + 6,928 + 64 = 10,528 |
| FLATTEN | 2 × 4 × 5 × 16 | 0 |
| DENSE | 640 | 641 |
| Total | | 14,421 |

Figure 3:
FIG. 3 is a graph of model performance quantified as areas under the curves (AUCs) of for one-year mortality predictions across all views with four different neural network architectures.

All four candidate architectures were applied to all the identified echocardiography views with a 1-year mortality label, and the 3D CNN consistently showed the best performance (FIG. 3). FIG. 3 is a graph of AUCs of one-year mortality predictions across all views with four different neural network architectures: 2D CNN+Global Average Pooling (GAP; dark gray), 2D CNN+Long Short-Term Memory (LSTM; light gray), a 3D CNN+GAP (light blue), and 3D CNN (dark blue).

Similarly, the performance gain was assessed at different image resolutions. The video resolution was reduced by factors of 2, 3, and 4. No consistent significant loss in performance was observed across all views (FIG. 4). Thus, it was decided to conduct all experiments with a resolution reduction by a factor of 4 to reduce computational cost.

To incorporate EHR data into the prediction, a three-layer multi-layer perceptron (MLP) with 10 hidden units at each layer was trained. Then, the last 10 hidden units with the CNN branch were concatenated (see FIG. 1).

Training Algorithm

The RMSProp algorithm was used to train the networks with LSTM coupling, and AdaGrad for the 3D CNN architectures. Each iteration of the 5-fold cross validation contained a training, validation, and test set. The training and test sets were sampled such that they had the same prevalence of alive patients, but the validation set was sampled with a balanced proportion. The validation set comprised 10% of the training set.

As the DNN was trained, the loss (binary cross-entropy) on the validation set was evaluated at each epoch. If the validation loss did not decrease for more than 10 epochs the training was stopped and the performance, in AUC, of the test set was reported. The maximum number of epochs was set to 1000 and kept the default training parameters as defined by the software Keras (version 2.2). Training always ended before the maximum number of epochs was reached.

Since the prevalence of each patient class is imbalanced (~16% deceased patients), the weights for each class were set as follows:

$$w_i = \frac{\text{Total Number of Samples}}{2(\text{Number of Samples in class } i)} \quad (1)$$

All training was performed in an NVIDIA DGX1 platform. Each fold was independently fit on each of the eight available GPUs. The main experiment, shown in FIG. 2, took a total of six days to complete.

Effect of Adding Optical Flow Inputs

Optical flow velocity maps have been shown to be informative along with the original videos for classification tasks. Thus, the dense optical flow vectors of the echocardiography raw videos were computed using the Gunnar Farneback's algorithm as implemented in the OpenCV (version 2.4.13.7) software library. The pyramid scale was set to 0.5, the number of levels to 3, and the window size to 5 pixels. The vectors were then converted to color videos where the color indicated direction (as in the HSV color space) and the brightness denoted amplitude. This resulted in an image video that was fed to the neural network model through an independent 3D CNN branch along with the raw video. As seen in FIG. 10, this combination of the optical flow video to the raw video did not yield consistently improved model performance compared with models using the raw video alone. Therefore, optical flow was not used for the final study analyses.

Use of Balanced Outcomes in the Cardiologist Survey Dataset

The 600-patient survey used to compare the accuracies of the cardiologists and the model, as described in the data pruning section, was intentionally balanced with respect to mortality outcomes (300 dead and 300 alive at one year) in order to ensure adequate power to detect differences in performance. The cardiologists were blinded to this distribution at the time of the review.

Software for Cardiologist Survey

Figure 11:
FIG. 11 is an interface of the web application developed for cardiologists to predict survival one year after echocardiography.

A web application was deployed with the interface shown in FIG. 11. FIG. 11 is an interface 20 of the web application developed for cardiologists to predict survival one year after echocardiography. The application required the cardiologist to input their institutional credentials for access. The 10 EHR variables and the two versions of the video, raw and annotated, were shown. The application then recorded the cardiologist prediction as they clicked on either the "Alive" or "Dead" buttons.

Statistical Analysis of Comparison Between Machine and Cardiologists

The cardiologists' responses were binary, and the Machine's response was continuous. 0.5 was set as the threshold for the Machine's response prior to performing the final comparison experiment. Since all responses were recorded for the same samples, a Cochran's Q test was conducted to assess whether the three responses where significantly different in the proportion of correctly classified samples. This test showed that there was enough evidence that at least one of the responses was significantly different with a p-value of 1.8e-15. A post hoc analysis of pairwise comparisons between the three responses resulted in Bonferroni-adjusted p-values of 0.003, $4.2e^{-11}$, and $6.9e^{-7}$ for the pairs Cardiologist 1 vs Cardiologist 2, Cardiologist 1 vs Machine, and Cardiologist 2 vs Machine, respectively.

Figure 12:
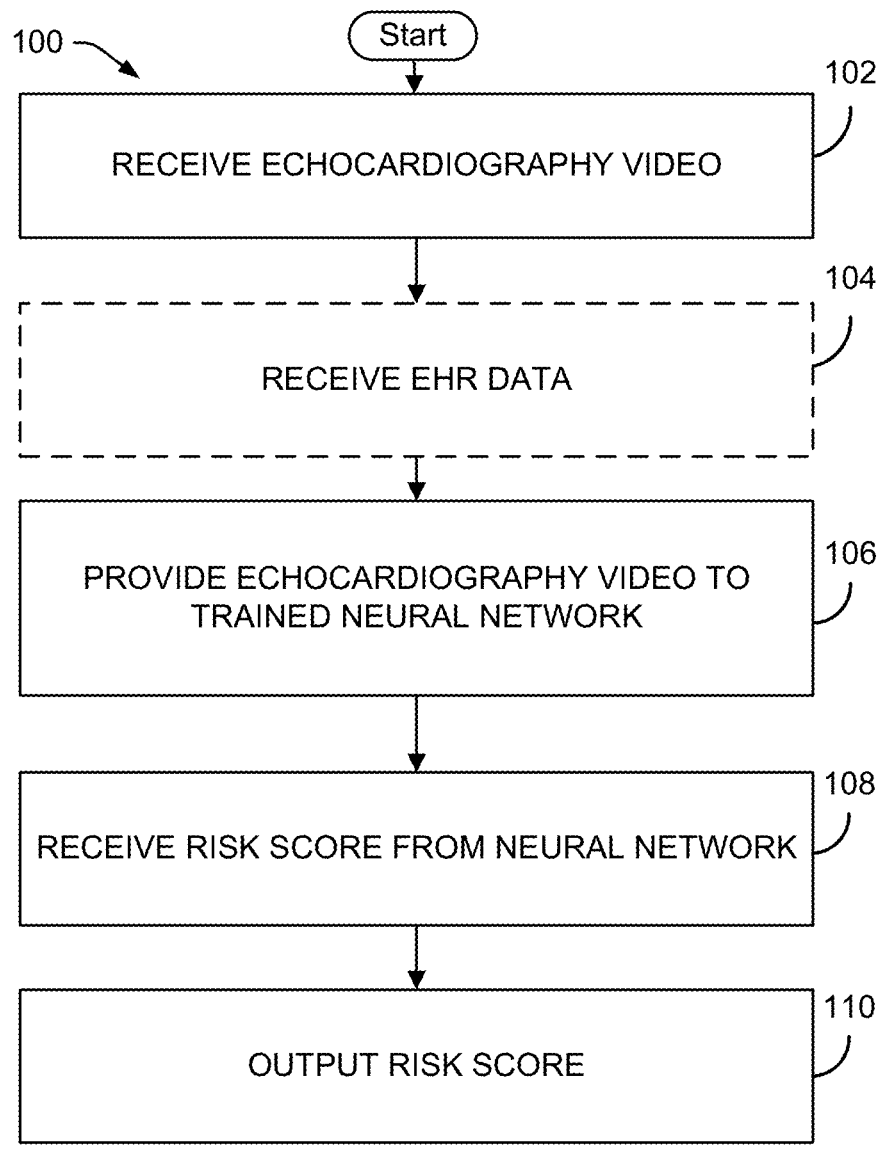
FIG. 12 is an exemplary process for predicting all-cause mortality in a patient for a predetermined time period (i.e., one year) based on echocardiography data as well as EHR data.

Turning now to FIG. 12 as well as FIG. 1, an exemplary process 100 for predicting a relevant clinical endpoint such as all-cause mortality in a patient for a predetermined time period (i.e., one year) based on a video of the heart (in this case echocardiography data) as well as any additional available EHR data is shown. The process 100 predicts a risk score for the patient based on a neural network, which can be a deep neural network such as a convolutional neural network, trained using videos of the heart such as echocardiogram videos and EHR variables as described above. The process 100 can be employed in a health analytics module that is used by a care team including the physician in order to treat the patient or for population level management of patients, for example a physician deploying resources to an entire population of ten thousand patients with heart failure. In some embodiments, the process 100 can be implemented as instructions (e.g., computer readable instructions) on at least one memory, and executed by one or more processors coupled to the at least one memory.

At 102, the process 100 can receive an echocardiographic video of a heart associated with a patient. The echocardiographic video can include echocardiography video frames. The video frames can include video frames taken from one or more views of the heart of the patient. For example, the video frames can include video frames taken at twenty-one different views of the heart. In some embodiments, the echocardiographic video can be associated with one or more echocardiographic views including an apical two-chamber view, an apical three-chamber view, an apical four-chamber view, an apical four-chamber focused to right ventricle view, an apical five chamber view, a parasternal long axis view, a parasternal long descending aorta view, a parasternal long mitral valve view, a parasternal long pulmonic valve view, a parasternal long right ventricle inflow view, a parasternal long zoom aortic valve view, a parasternal short aortic valve view, a parasternal short pulmonic valve and pulmonary artery view, a parasternal short tricuspid valve view, a short axis apex view, a short axis base view, a short axis mid papillary view, a subcostal four-chamber view, a subcostal hepatic vein view, a subcostal inter-atrial septum view, a subcostal inferior vena cava view, a subcostal right ventricle view, a suprasternal notch view, a short axis mid papillary view, a short axis apex view, an apical three-chamber zoom view, an apical two-chamber zoom view, and/or a short axis base view. In some embodiments, the echocardiographic video can be associated with a single view of the heart. In some embodiments, the single view can be the parasternal long axis view. The parasternal long axis view has been shown to outperform other single views as described above. The process 100 can then proceed to 104.

At 104, the process 100 can receive EHR data including a number of values of parameters associated with the patient. The EHR data is optional, and in some embodiments, the process 100 may only receive echocardiographic video at 102. Using EHR data can improve the performance of risk score generation. In some embodiments, the parameters can include age, tricuspid regurgitation maximum velocity, heart rate, low density lipoprotein [LDL], left ventricular ejection fraction, diastolic pressure, pulmonary artery acceleration time, systolic pressure, pulmonary artery acceleration slope, and diastolic function. In some embodiments, the variables can include at least a portion of the variables listed in Table 3 above. In some embodiments, the EHR data can include values of a number of parameters including demographic parameters, vitals parameters, laboratory measurement parameters, echocardiogram-based parameters, and diagnosis parameters. The values can be associated with the patient. In some embodiments, the demographic parameters can include age, sex, and/or smoking status. In some embodiments, the vitals parameters can include height, weight, heart rate, diastolic blood pressure, and systolic blood pressure. In some embodiments, the laboratory measurement parameters can include comprising low-density lipoprotein level and/or high-density lipoprotein level. In some embodiments, the echocardiogram-based parameters can include physician-reported left ventricular ejection fraction, aortic insufficiency deceleration slope, aortic insufficiency maximum velocity, velocity-time integral of distal to aortic valve flow, maximum velocity of distal to aortic valve flow, mean velocity of distal to aortic valve flow, aortic root diameter, ascending aortic diameter, Iv end-diastolic volume: apical 2-chamber, Iv end-diastolic volume: apical 4-chamber, Iv end-diastolic volume: apical 2-chamber, Iv end-diastolic volume: apical 4-chamber, Iv end-systolic volume: apical 2-chamber, Iv end-systolic volume: apical 4-chamber, Iv end-systolic volume: apical 2-chamber, Iv end-systolic volume: apical 4-chamber, iv septum dimension at end-diastole, left atrium dimension, left atrium volume derived from apical 2-chamber, left atrium volume derived from apical 4-chamber, velocity-time integral proximal to the obstruction, maximum Iv velocity proximal to the obstruction, mean Iv velocity proximal to the obstruction, Iv area at end-diastole derived from apical 2-chamber, Iv area at end-diastole derived from apical 4-chamber, Iv area at end-systole derived from apical 2-chamber, Iv area at end-systole derived from apical 4-chamber, Iv internal dimension at end-diastole, Iv internal dimension at end-systole, Iv long-axis length at end-diastole derived from apical 2-chamber, Iv long-axis length at end-diastole derived from apical 4-, chamber, Iv long-axis length at end systole derived from apical 2-, chamber, Iv long-axis length at end systole derived from apical 4-chamber, Iv outflow tract area, Iv outflow tract diameter, Iv posterior wall thickness at end-diastole, mitral regurgitation maximum velocity, a-point maximum velocity of mitral flow, e-point maximum velocity of mitral flow, maximum velocity of mitral valve flow, mitral valve deceleration slope, mitral valve deceleration time, maximum velocity of distal to pulmonic valve flow, pulmonary artery acceleration slope, pulmonary artery acceleration time, pulmonary r-r time interval, right atrial end-systolic mean pressure, right ventricle dimension at end-diastole, tricuspid regurgitation maximum velocity, aortic valve regurgitation, mitral valve regurgitation, tricuspid valve regurgitation, pulmonary valve regurgitation, aortic valve stenosis, mitral valve stenosis, tricuspid valve stenosis, pulmonary valve stenosis, and/or physician-reported diastolic function. In some embodiments, the diagnosis parameters can include diagnosis of acute rheumatic fever, diagnosis of chronic rheumatic heart disease, diagnosis of hypertensive diseases, diagnosis of ischemic heart diseases, diagnosis of pulmonary heart disease and diseases of pulmonary circulation, diagnosis of acute pericarditis, diagnosis of other forms of heart disease, diagnosis of acute myocarditis, diagnosis of cardiomyopathy, diagnosis of cardiac arrest, diagnosis of paroxysmal tachycardia, diagnosis of atrial fibrillation, diagnosis of heart failure, diagnosis of cerebrovascular diseases, diagnosis of diseases of arteries, arterioles and capillaries, diagnosis of diseases of veins, lymphatic vessels, and lymph nodes, diagnosis of hypotension, diagnosis of other and unspecified disorders of the circulatory system, diagnosis of diabetes mellitus, diagnosis of congenital heart defect, diagnosis of dyslipidemia, and/or diagnosis of chronic kidney disease. In some embodiments, the diagnosis parameters can be parameters included in predetermined guidelines such as cMERGE. The process 100 can then proceed to 106.

At 106, the process 100 can provide the video frames to the trained neural network. In some embodiments, the process 100 can provide the video frames and the HER data to the trained neural network. As described above, the trained neural network can be a convolutional neural network. In some embodiments, the trained neural network can be the neural network architecture 10 shown in FIG. 1. In some embodiments, the trained neural network can be trained based on a training dataset including a plurality of videos, each video included on the plurality of videos being associated with an echocardiographic view included in a number of echocardiographic views. The number of echocardiographic views can include one or more views. In some embodiments, the number of echocardiographic views can include at least one of an apical two-chamber view, an apical three-chamber view, an apical four-chamber view, an apical four-chamber focused to right ventricle view, an apical five chamber view, a parasternal long axis view, a parasternal long descending aorta view, a parasternal long mitral valve view, a parasternal long pulmonic valve view, a parasternal long right ventricle inflow view, a parasternal long zoom aortic valve view, a parasternal short aortic valve view, a parasternal short pulmonic valve and pulmonary artery view, a parasternal short tricuspid valve view, a short axis apex view, a short axis base view, a short axis mid papillary view, a subcostal four-chamber view, a subcostal hepatic vein view, a subcostal inter-atrial septum view, a subcostal inferior vena cava view, a subcostal right ventricle view, a suprasternal notch view, a short axis mid papillary view, a short axis apex view, an apical three-chamber zoom view, an apical two-chamber zoom view, or a short axis base view. The training dataset can further include a plurality of survival outcomes, each video included on the plurality of videos being associated with a survival outcome included in the plurality of survival outcomes. In this way, the neural network can be trained based on real patient outcomes. In some embodiments, the training dataset can further include an electronic health record dataset, each video included on the plurality of videos being associated with a portion of the electronic health record dataset. In some embodiments, the electronic health record dataset can be associated with a number of patients and can include values of a number of parameters including age, tricuspid regurgitation maximum velocity, heart rate, low density lipoprotein, left ventricular ejection fraction, diastolic pressure, pulmonary artery acceleration time, systolic pressure, pulmonary artery acceleration slope, and diastolic function. As described above, these parameters have been shown to perform well these ten parameters have been shown to provide good predictive power.

In some embodiments, the electronic health record dataset can include values of a number of parameters including demographic parameters, vitals parameters, laboratory measurement parameters, echocardiogram-based parameters, and diagnosis parameters. In some embodiments, the demographic parameters can include age, sex, and/or smoking status. In some embodiments, the vitals parameters can include height, weight, heart rate, diastolic blood pressure, and systolic blood pressure. In some embodiments, the laboratory measurement parameters can include comprising low-density lipoprotein level and/or high-density lipoprotein level. In some embodiments, the echocardiogram-based parameters can include physician-reported left ventricular ejection fraction, aortic insufficiency deceleration slope, aortic insufficiency maximum velocity, velocity-time integral of distal to aortic valve flow, maximum velocity of distal to aortic valve flow, mean velocity of distal to aortic valve flow, aortic root diameter, ascending aortic diameter, Iv end-diastolic volume: apical 2-chamber, Iv end-diastolic volume: apical 4-chamber, Iv end-diastolic volume: apical 2-chamber, Iv end-diastolic volume: apical 4-chamber, Iv end-systolic volume: apical 2-chamber, Iv end-systolic volume: apical 4-chamber, Iv end-systolic volume: apical 2-chamber, Iv end-systolic volume: apical 4-chamber, iv septum dimension at end-diastole, left atrium dimension, left atrium volume derived from apical 2-chamber, left atrium volume derived from apical 4-chamber, velocity-time integral proximal to the obstruction, maximum Iv velocity proximal to the obstruction, mean Iv velocity proximal to the obstruction, Iv area at end-diastole derived from apical 2-chamber, Iv area at end-diastole derived from apical 4-chamber, Iv area at end-systole derived from apical 2-chamber, Iv area at end-systole derived from apical 4-chamber, Iv internal dimension at end-diastole, Iv internal dimension at end-systole, Iv long-axis length at end-diastole derived from apical 2-chamber, Iv long-axis length at end-diastole derived from apical 4-, chamber, Iv long-axis length at end systole derived from apical 2-, chamber, Iv long-axis length at end systole derived from apical 4-chamber, Iv outflow tract area, Iv outflow tract diameter, Iv posterior wall thickness at end-diastole, mitral regurgitation maximum velocity, a-point maximum velocity of mitral flow, e-point maximum velocity of mitral flow, maximum velocity of mitral valve flow, mitral valve deceleration slope, mitral valve deceleration time, maximum velocity of distal to pulmonic valve flow, pulmonary artery acceleration slope, pulmonary artery acceleration time, pulmonary r-r time interval, right atrial end-systolic mean pressure, right ventricle dimension at end-diastole, tricuspid regurgitation maximum velocity, aortic valve regurgitation, mitral valve regurgitation, tricuspid valve regurgitation, pulmonary valve regurgitation, aortic valve stenosis, mitral valve stenosis, tricuspid valve stenosis, pulmonary valve stenosis, and/or physician-reported diastolic function. In some embodiments, the diagnosis parameters can include diagnosis of acute rheumatic fever, diagnosis of chronic rheumatic heart disease, diagnosis of hypertensive diseases, diagnosis of ischemic heart diseases, diagnosis of pulmonary heart disease and diseases of pulmonary circulation, diagnosis of acute pericarditis, diagnosis of other forms of heart disease, diagnosis of acute myocarditis, diagnosis of cardiomyopathy, diagnosis of cardiac arrest, diagnosis of paroxysmal tachycardia, diagnosis of atrial fibrillation, diagnosis of heart failure, diagnosis of cerebrovascular diseases, diagnosis of diseases of arteries, arterioles and capillaries, diagnosis of diseases of veins, lymphatic vessels, and lymph nodes, diagnosis of hypotension, diagnosis of other and unspecified disorders of the circulatory system, diagnosis of diabetes mellitus, diagnosis of congenital heart defect, diagnosis of dyslipidemia, and/or diagnosis of chronic kidney disease. In some embodiments, the diagnosis parameters can be parameters included in predetermined guidelines such as cMERGE. The process 100 can then proceed to 108.

At 108, the process 100 can receive a risk score from the trained neural network. The risk score can be associated with a risk of a clinical outcome for the patient. In some embodiments, the risk score can be a mortality risk score. In some embodiments, the mortality risk score can be an all-cause mortality risk score. In some embodiments, the mortality risk score associated with the patient can provide sufficient information to the medical practitioner or healthcare administrator for the medical practitioner or healthcare administrator to make a determination about a potential treatment for the patient. In some embodiments, the potential treatment can include cardiac transplantation, implantation of mechanical support devices, defibrillator placement, palliative care, and/or hospice. In some embodiments, the determination can be eligibility for the potential treatment. The process 100 can then proceed to 110.

At 110, the process 100 can output the raw risk score to at least one of a memory or a display for viewing by a medical practitioner or healthcare administrator. In some embodiments, the process 100 can generate and output a report based on the risk score. The report can include the raw risk score. The report can include any appropriate graphs and/or charts generated based on the risk score. The report can be displayed to a physician using a display such as a computer monitor or a screen integral to a tablet computer, smartphone, laptop computer etc. In some embodiments, the report can be output to a storage device including a memory. In some embodiments, the report can include information about potential treatments for the patient and/or links to information about the potential treatments for the patient. In some embodiments, the links can be hyperlinks. In some embodiments, the potential treatments for the patient can include cardiac transplantation, implantation of mechanical support devices, defibrillator placement, palliative care, and/ or hospice. In some embodiments, a medical practitioner may make a determination (e.g., an eligibility determination) for the patient based on the report.

Figure 13:
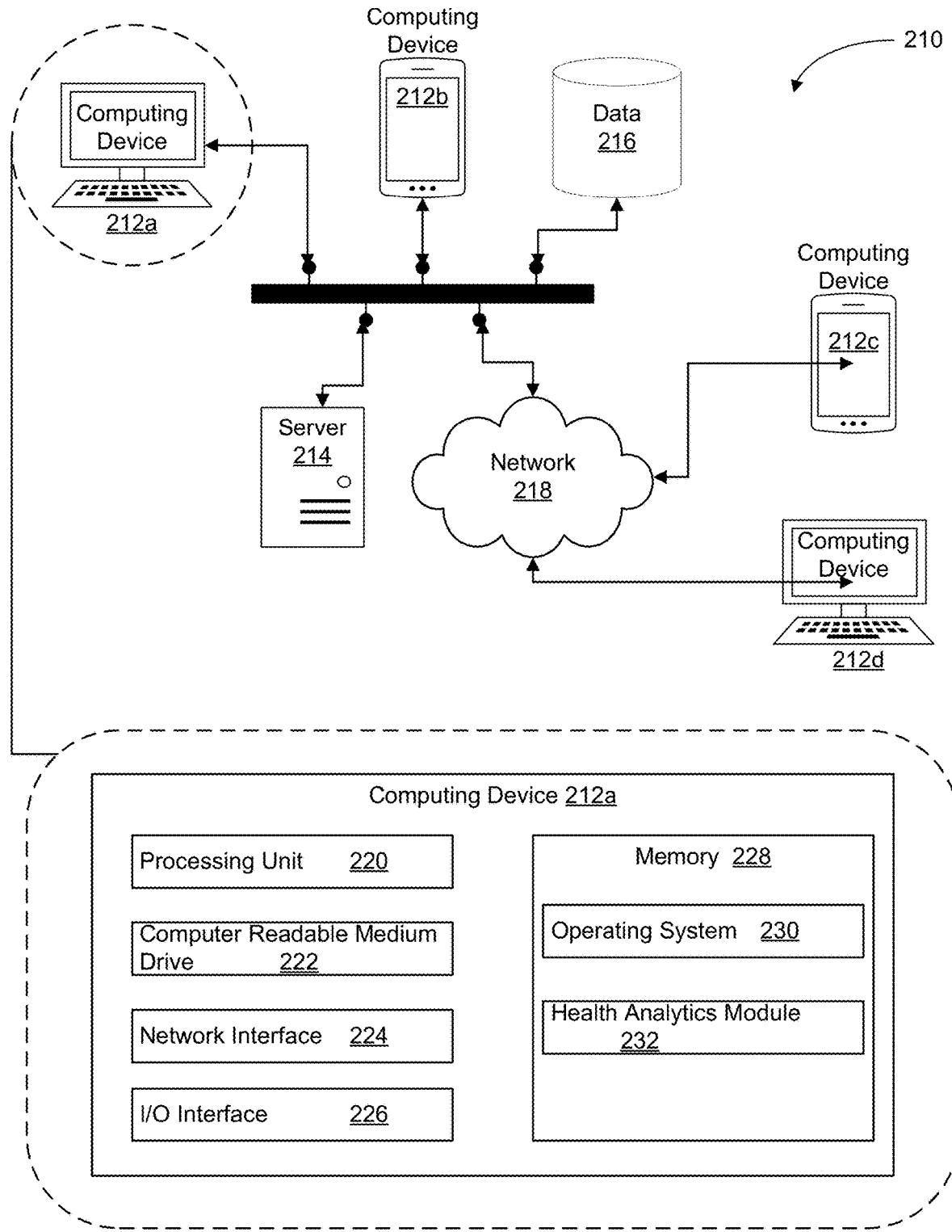
FIG. 13 is an exemplary system for implementing the aforementioned disclosure.

Turning now to FIG. 13, an exemplary system 210 for implementing the aforementioned disclosure is shown. The system 210 may include one or more computing devices 212a, 212b in communication with one another, as well as with a server 214 and one or more databases or other data repositories 216, e.g., via Internet, intranet, Ethernet, LAN, WAN, etc. The computing devices also may be in communication with additional computing devices 212c, 212d through a separate network 218. Although specific attention is paid to computing device 212a, each computing device may include a processor 220, one or more computer readable medium drive 222, a network interface 224, and one or more I/O interfaces 226. The device 212a also may include memory 228 including instructions configured to cause the processor to execute an operating system 230 as well as a health analytics module 232 for predicting important clinical endpoints such as all-cause mortality in a patient for a predetermined time period (i.e., one year) based on video data such as echocardiography data as well as EHR data as described herein. The health analytics module 232 can be used to execute at least a portion of the process 100 described above in conjunction with FIG. 12.

Additional examples of techniques for generating risk scores (e.g., mortality risk scores), progression-free survival (PGS) scores, etc. based on echocardiogram videos are now described. First, experiments used to design network architectures for trained models are described. Further below, the performance of the trained models is compared against other techniques.

Model Design

Electronic Health Records Data Preprocessing

The institutional echocardiography archives used included, as of January 2020, a total of 683,662 echocardiography studies from 305,282 unique patients collected over the prior 22 years. All structured physician-reported echocardiography-derived measurements (n=58) were extracted from these studies. Furthermore, through an institutional phenomics initiative database, the echocardiography-derived measurements were linked to patient demographics (3), vitals (5), laboratory (2), and problem list data (90; International Classification of Diseases, Tenth Revision (ICD10) codes) from an institutional EHR (Epic Systems; 1996—present). Table 3 above shows a list and description of all 158 "EHR variables" used in the study.

All continuous variables were cleaned to remove physiologically out-of-limit values (manually defined by a cardiologist), which were presumed to reflect input errors, and set as missing. Eight categorical variables were identified in the echocardiography measurements that each reported five valvular regurgitation and stenosis severity levels (including not assessed) and converted them to forty one-hot encoded binary variables. An ordinal variable reporting diastolic function was also identified and coded it as 1 for normal, 0 for dysfunction (but no grade reported), and 1, 2 and 3 for diastolic dysfunction grades I, II, and III, respectively. For non-echocardiography-derived measurements, such as LDL, HDL, blood pressure, heart rate (if not taken at the study), weight, and height measurements, the most recent past measurement was retrieved, within a 1-year window, relative to the echocardiogram acquisition date.

The patient's age and survival duration was calculated as of the date of the echocardiogram. The patient status (dead or alive) was identified based on the last known living encounter or confirmed death date, which is cross-referenced monthly in against national death index databases. For labeling one-year mortality, a positive sample was defined as an echocardiography study within one year of the patient's death date. A negative one-year mortality label was defined as an echocardiography study that occurred more than one year before the death date (if deceased) or last known physical encounter within the system (if alive). Studies without a death date or at least one-year follow-up (physical encounter) were excluded.

Image Collection and Preprocessing

An echocardiography study consists of several videos containing multiple views of the heart. The retrieved DICOM files contained an annotated video and a raw video when the equipment was configured to store it. The raw video contained only the beam-formed ultrasound image stored in a stream of bytes format, whereas the annotated video contained annotations (such as the view name) on top of the raw video as shown in FIGS. 8A and 8B. Raw videos were used for all analyses. Since the videos in raw format varied in frame rate across studies, all videos were linearly interpolated to thirty frames per second.

Along with the video data, the DICOM file included tags that labelled each video indicating the specific image orientation in which it was acquired, which can be referred to as a "view." These view tags had slight variations across studies for the same type of view. For example, an apical four chamber view could be tagged as "a4", "a4 2d", or "ap4". Samples of each unique tag were visually inspected and grouped into common views as shown in Table 9. For the entire cross-validation cohort, the average number of views available for negative samples was 19.4, the interquartiles were 19 and 22. For positive samples, the average was 18.3 videos, and interquartiles were 18 and 22 videos per sample. The median number of videos was 20 for both positive and negative samples. When a study had multiple videos from the same view, the video with the longest duration was selected.

TABLE 9

| | | |
|---|---|---|
| A2 | Apical 2 | a2, ap2 2d, a2 2d, a2 lavol, la 2ch |
| A LONG | Apical 3 | a long, ap3 2d, a3 2d |
| AP4 | Apical 4 | ap4, ap4 2d, a4 2d, a4 zoom, a4 lavol, la ap4 ch |
| RV FOCUS | Apical 4 focused to rv | rv focus, rvfocus |
| A5 | Apical 5 | a5, ap5 2d, a5 2d |
| PL DEEP | Parasternal long axis | pl deep, psl deep |
| PL ASCAO | Parasternal long ascending aorta | pl ascao, asc ao, pl asc ao |
| PLA MV | Parasternal long mitral valve | pla mv |
| PL PV | Parasternal long pulmonic valve | pl pv, pv lax |
| PL RVIF | Parasternal long rv inflow | pl rvif, rv inf, rvif 2d |
| PL AV AO | Parasternal long zoom aortic valve | pl av ao, av zoom |
| PS AV | Parasternal short aortic valve | ps av, psavzoom, psax av |
| PS PV PA | Parasternal short pulmonic valve and pulmonary artery | ps pv pa, ps pv, psax pv |
| PS TV | Parasternal short tricuspid valve | ps tv, ps tv 2d, psax tv |
| SAX APEX | Short axis apex | sax apex |
| LV BASE | Short axis base | lv base |
| SAX MID | Short axis mid papillary | sax mid, sax |
| SBC 4 CH | Subcostal 4 chamber | sbc 4 ch, sbc 4, sbc 4ch |
| IVC HV | Subcostal hepatic vein | ivc hv, sbc hv |
| IAS | Subcostal inter-atrial septum | ias, sbc ias, ias 2d |

TABLE 9-continued

| | | |
|---|---|---|
| IVC RESP | Subcostal ivc with respiration | ivc resp, sbc ivc, ivc insp, ivc snif, ivcsniff, sniff |
| SBC RV | Subcostal rv | sbc rv |
| SSN | Suprasternal notch | ssn, ssn sax |
| LV MID | Short axis mid papillary | lv mid |
| LV APEX | Short axis apex | lv apex |
| SAX BASE | Short axis base | sax base |

Since each video from a view group could potentially have different dimensions, all videos were normalized to the most common row and column dimension pairs of its corresponding view. Each frame was cropped or padded with zeros to match the most common dimensions among the view group, keeping the beam-formed image centered. It is noted that the image size normalization (cropping and padding) had a minimal effect on the video because the standard echocardiography views center the anatomical region of interest. For example, less than 3% of the PL DEEP videos were cropped and padded more than six rows, from which only seventeen cases were cropped and the rest were zero padded. Generally, border areas did not contain features of interest.

Data Selection

Echocardiography studies were extracted from clinical imaging archives (acquired after February 2011) to research servers for this analysis, and only raw video data was retained from these studies, as available. This extracted subset of the total clinical archive was divided into three distinct groups to conduct the experiments described above (the characteristics of each are described in Table 10 below). In each case, follow-up beyond one year or date of death within one year was known.

3. Heart Failure Experiment:

This experiment included 3,384 studies with 58,561 videos collected from 2,404 patients, specifically selected from the clinical archive based on the presence of heart failure—based on the "definite" eMERGE algorithm criteria—at the time of the echocardiogram. The 42,095 studies in the cross-validation set are a subset of a previously published cohort.

Cardiologist Survey

As described above, ten of the most predictive clinical ("EHR") variables for 1-year mortality following an echocardiogram are age, tricuspid regurgitation maximum velocity, heart rate, low density lipoprotein, left ventricular ejection fraction, diastolic pressure, pulmonary artery acceleration time, systolic pressure, pulmonary artery acceleration slope, and diastolic function. For the sake of assessing the cardiologists' performances in an efficient manner, the top ten variables as a summary of the patient's status as of the day of the echocardiogram. Along with these ten measurements, a parasternal long-axis video was also presented. This view is typically reported by cardiologists as the most informative "summary" view of overall cardiac health because it contains elements of the left ventricle, left atrium,

TABLE 10

| | Cross Validation | | | Survey | | | Heart Failure | | |
|---|---|---|---|---|---|---|---|---|---|
| | All | Alive | Deceased | All | Alive | Deceased | All | Alive | Deceased |
| Count | 42,095 | 35,963 | 6,132 | 600 | 300 | 300 | 3,384 | 2,435 | 949 |
| Demographics | | | | | | | | | |
| Male | 51.30% | 50.60% | 55.50% | 55.50% | 53.30% | 57.70% | 55.70% | 56.30% | 54.20% |
| Age | 65.7(16.4) | 64.4(16.4) | 73.5(13.8) | 68.4(16.2) | 63.2(17.2) | 73.7(13.2) | 73.4(12.9) | 71.8(13.0) | 77.6(11.4) |
| LV Ejection Fraction | 54.7(11.3) | 55.4(10.4) | 50.9(15.0) | 53.5(12.8) | 55.3(10.5) | 51.7(14.5) | 45.2(15.6) | 46.0(15.1) | 43.2(16.7) |
| BMI | 30.8(8.0) | 31.1(7.9) | 29.1(8.3) | 30.0(8.2) | 31.3(8.5) | 28.7(7.6) | 31.6(8.4) | 32.3(8.4) | 29.8(8.2) |
| Co-morbidities | | | | | | | | | |
| Heart Failure | 13.50% | 10.40% | 31.30% | 21.50% | 11.30% | 31.70% | 100% | 100% | 100% |
| Hypertension | 72.70% | 73.40% | 68.30% | 70.00% | 73.70% | 66.30% | 85.80% | 87.30% | 82.00% |
| Type 11 Diabetes Mellitus | 29.60% | 28.80% | 33.80% | 31.70% | 29.30% | 34.00% | 47.30% | 47.10% | 47.70% |

1. Cross-Validation Experiment:

This experiment includes 42,095 studies with 812,278 videos collected from 34,362 patients, drawn without pre-defined patient selection criteria from the clinical echocardiography archive.

2. Cardiologist Surveys:

These surveys included 600 studies with 11,357 videos collected from 600 unique patients, again taken from the unselected clinical data extraction but held out from the cross-validation experiment set and pre-specified to have balanced outcome labels (three hundred dead and three hundred alive at one year).

right ventricle, aortic and mitral valves, and whether or not there is a pericardial or left pleural effusion all within a single view.

Following a sample size calculation (Pearson Chi-square test) to estimate and compare prognostic accuracy between the cardiologists and the model, the cardiologists completed a survey set of 600 samples. A 10% difference in accuracy between machine and cardiologist (80% vs 70%), 80% power, a significance level of 5%, and an approximate 40% discordancy were assumed. The calculation (performed with Power Analysis Software PASS v15) showed that at least 600 patients (three hundred alive, three hundred deceased)

were needed. Thus, three hundred positive and three hundred negatives studies were randomly sampled that contained a parasternal long-axis view, ensuring that none of these patients remained in the cross-validation set.

Figure 14:
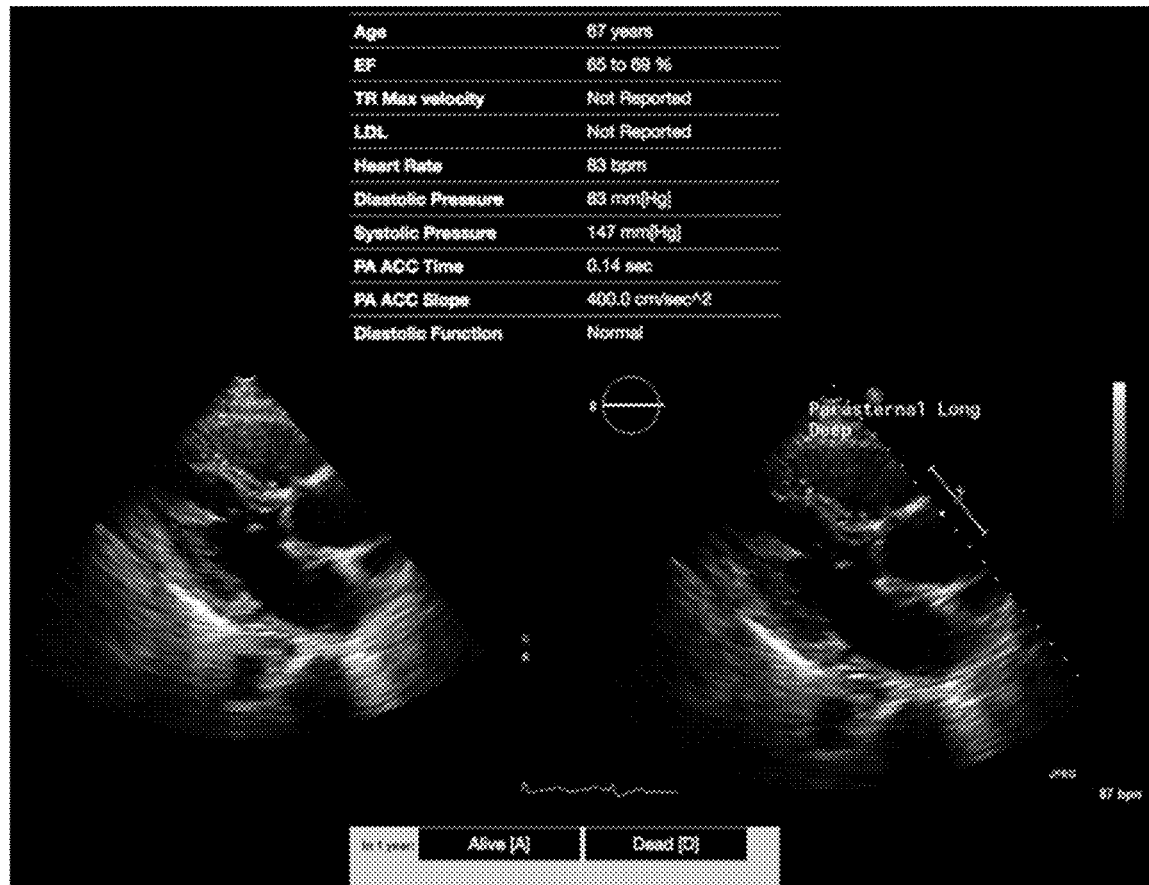
FIG. 14 is an exemplary interface for a first survey.

The first survey presented one patient sample at a time and was designed to score the cardiologists' aggregated discrimination ability. FIG. 14 illustrates the interface for the first survey. The ten EHR variables were displayed in a table two versions of the video, raw and annotated. The application then recorded the cardiologist prediction as they clicked on either the "Alive" or "Dead" buttons.

Figure 15:
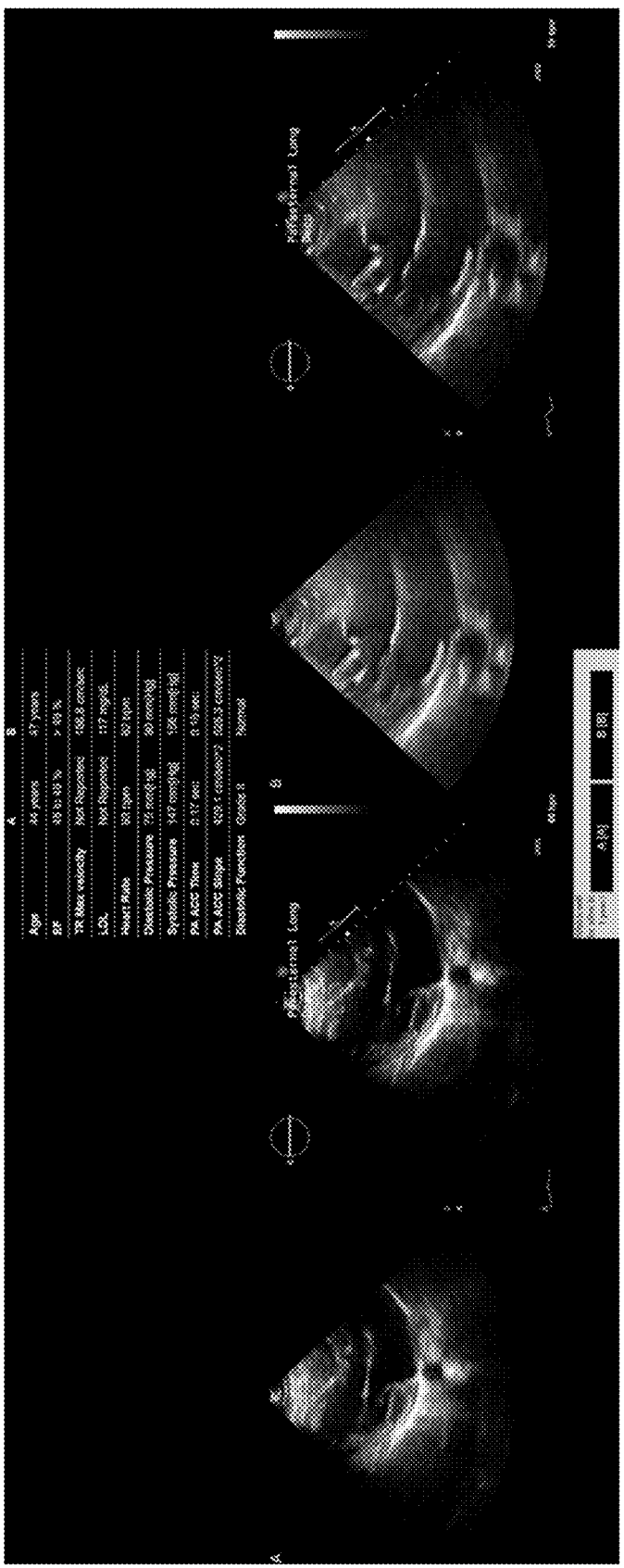
FIG. 15 is an interface for a paired survey.

The second survey presented paired samples and was designed to assess the discrimination ability of each cardiologist while controlling for mortality prevalence. Three hundred pairs were prepared based on sex, age (within 5 years) and left ventricular EF (within 10%). All three hundred positive cases were paired to a negative case, where two hundred and thirteen negatives were unique and the remaining eighty-seven pairs had to contain already used negatives in order to preserve the matching criteria. Thus, all positive cases were unique. FIG. 15 shows the interface for the paired survey, where the video was shown and 10 EHR variables for two age, sex, and EF-matched patients.

The third and last survey presented individual samples followed by the same sample with additional information extracted from the DNN model. The machine score and occlusion maps were presented to assess whether the inclusion of machine information could improve the cardiologist aggregated score performance. The same six hundred patients were presented twice. First, the individual sample was displayed as shown in FIG. 14 and, immediately after, the same sample was shown with the calibrated risk score from the model and occlusion map. The cardiologists then either amended or reiterated their prediction.

Figure 16:
FIG. 16 is an interface for a model assisted portion of a third survey.

In order to avoid incremental performance changes while the cardiologists progressed through the survey, the cardiologists were presented, prior to taking the survey, with eighty examples with machine predictions, occlusion maps, and true outcomes from the cross-validation set. The eighty examples were distributed in four groups of twenty, grouped by history of heart failure only, history of myocardial infarction only, history of both, or history of neither. Each of the four groups were further split into five examples that fell into each of the four quadrants of the confusion matrix. FIG. 16 shows the interface for the model assisted portion of the third survey, where a "Machine Prediction" row and an occlusion map video were added.

It is noted that no individual patient-level response feedback was presented to the cardiologists between any surveys (to avoid confounding results of subsequent surveys from knowledge gained through prior surveys) and a minimum of fifteen days elapsed between surveys for a given cardiologist.

Neural Network Architectures

Four different low-parameter architectures are now presented: 1) A time-distributed two-dimensional Convolutional Neural Network (2D CNN) with LSTM, 2) a time-distributed 2D CNN with Global Average Pooling (GAP), 3) a 3D CNN, and 4) a 3D CNN with GAP. For simplicity, the four candidate architectures are abbreviated as 2D CNN+LSTM, 2D CNN+GAP, 3D CNN, and 3D CNN+GAP.

Figure 17:
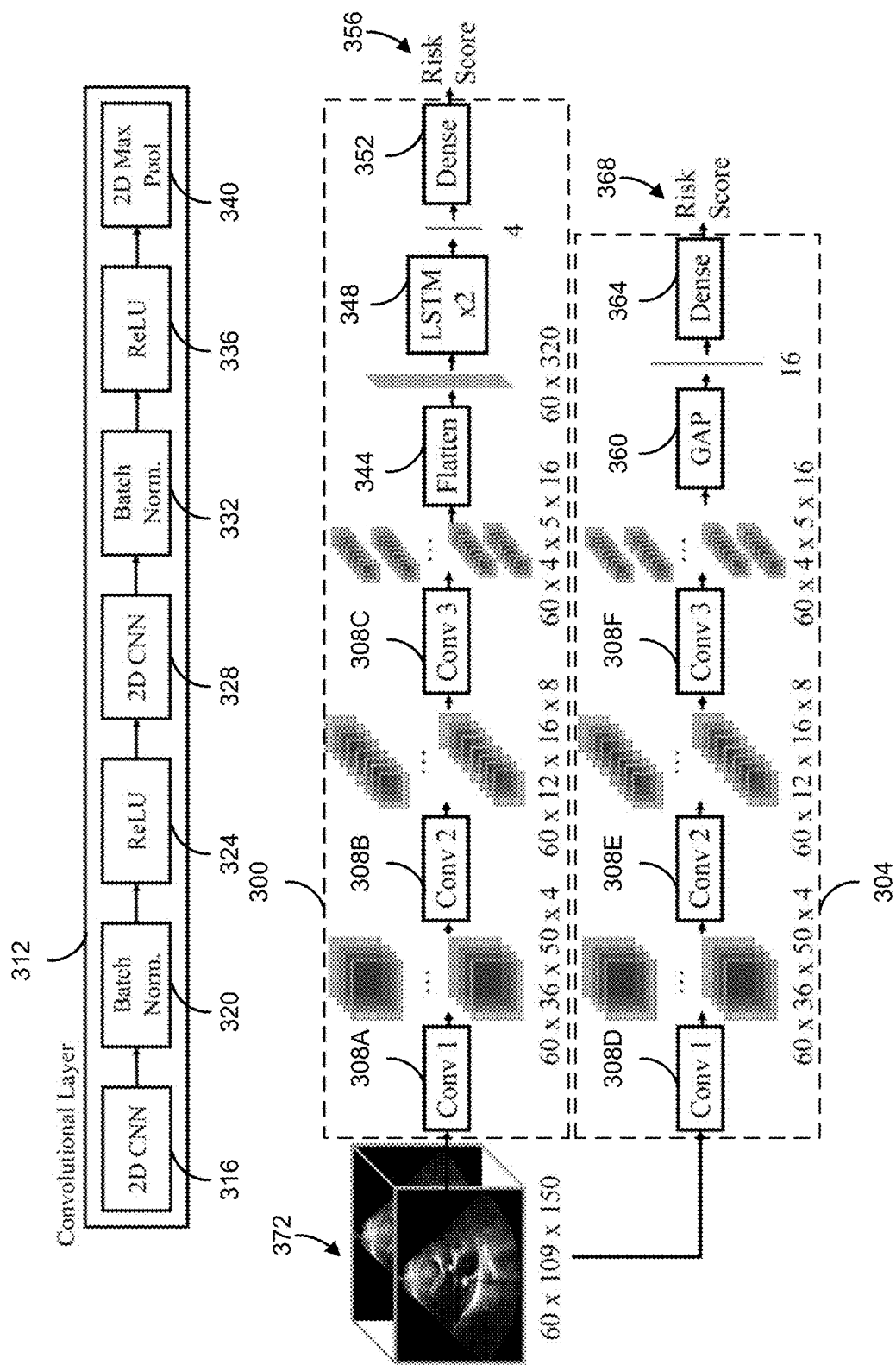
FIG. 17 is an exemplary first model and an exemplary second model.

FIG. 17 illustrates a first model 300 and a second model 304. The first model 300 can be a 2D CNN with LSTM. The second model 304 can be a 2D CNN with GAP. Both the first model 300 and the second model 304 can include a number of convolutional layers 308A-F. An exemplary convolutional layer 312 is shown that can be used as any of the convolutional layers 308A-F. In some embodiments, the convolutional layer 312 can include a first 2D CNN layer 316, a first batch normalization 320, a first ReLU 324, a second 2D CNN layer 328, a second Batch Normalization 332, a second ReLU 336, and a 2D Max Pooling layer 340. In some embodiments, kernel dimensions of the first model 300 and the second model 304 can be three, and the 2D Max Pooling layer 340 can be applied in a 3×3 window. In some embodiments, kernel dimensions of the first model 300 and the second model 304 can be five, and the 2D Max Pooling layer 340 can be applied in a 5×5 window.

The first model 300 can include a flatten layer 344, an LSTM layer 348, and a dense layer 352 that outputs a risk score 356. In some embodiments, the LSTM layer 348 can include two LSTM units. The risk score 356 output by the first model 300 can be referred to as a video risk score. The second model 304 can include a GAP layer 360 and a dense layer 364 that outputs a risk score 368. The risk score 368 output by the second model 304 can be referred to as a video risk score. Exemplary video dimensions are shown for an input video 372 that the first model 300 and/or the second model 304 can receive. It is understood that certain layer sizes and/or video sized can be adjusted depending on an application using the first model 300 and/or the second model 304.

Figure 18:
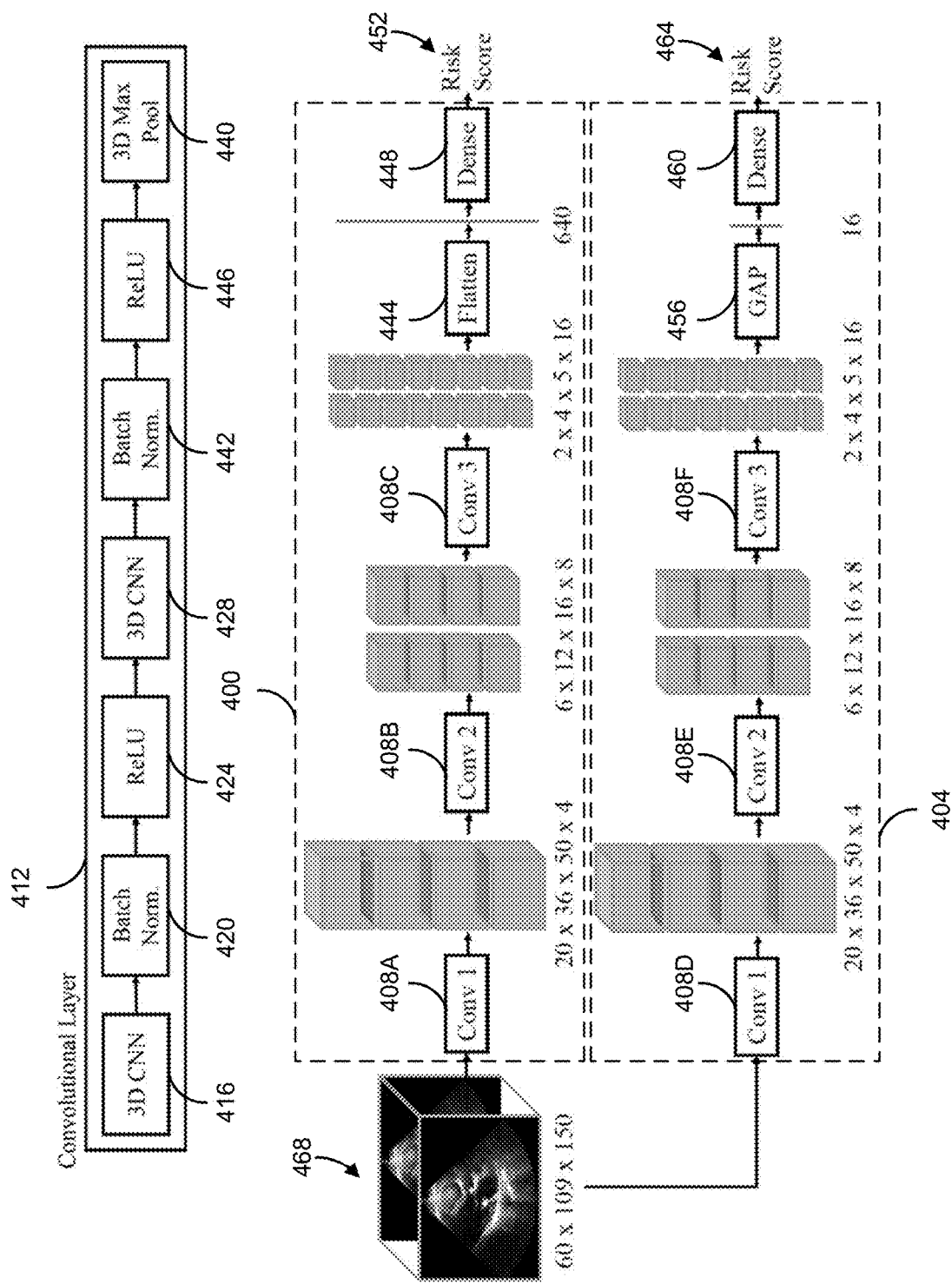
FIG. 18 is an exemplary third model and an exemplary fourth model.

FIG. 18 illustrates a third model 400 and a fourth model 404. The third model 400 can be a 3D CNN. The fourth model 404 can be a 3D CNN with GAP. Both the third model 400 and the fourth model 404 can include a number of convolutional layers 408A-F. An exemplary convolutional layer 412 is shown that can be used as any of the convolutional layers 408A-F. In some embodiments, the convolutional layer 412 can include a first 3D CNN layer 416, a first batch normalization 420, a first ReLU 424, a second 3D CNN layer 428, a second Batch Normalization 432, a second ReLU 436, and a 3D Max Pooling layer 440. In some embodiments, kernel dimensions of the third model 400 and the fourth model 404 can be three, and the 3D Max Pooling layer 440 can be applied in a 3×3 window. In some embodiments, kernel dimensions of the third model 400 and the fourth model 404 can be five, and the 3D Max Pooling layer 440 can be applied in a 5×5 window.

The third model 400 can include a flatten layer 444 and a dense layer 448 that outputs a risk score 452. The risk score 452 output by the third model 400 can be referred to as a video risk score.

The fourth model 404 can include a GAP layer 456 and a dense layer 460 that outputs a risk score 464. The risk score 464 output by the fourth model 404 can be referred to as a video risk score. Exemplary video dimensions are shown for an input video 468 that the third model 400 and/or the fourth model 404 can receive. It is understood that certain layer sizes and/or video sized can be adjusted depending on an application using the third model 400 and/or the fourth model 404.

In some embodiments, the first model 300, the second model 304, the third model 400, and/or the fourth model 404 can be neural networks (e.g., convolutional neural networks and/or deep neural networks). Exemplary parameter and layer information for the first model 300, the second model 304, the third model 400, and the fourth model 404 are shown in Tables 11, 12, 13, and 14, respectively, below.

TABLE 11

| Layer | # Parameters | Output Shape | Description |
|---|---|---|---|
| Convolutional Layer 1 | | | |
| Conv 1.1 | 40 | [60, 109, 150, 4] | 4 2D feature maps |
| BN + ReLU | 16 | [60, 109, 150, 4] | Normalize feature maps |
| Conv 1.2 | 148 | [60, 109, 150, 4] | 4 2D feature maps |
| BN + ReLU | 16 | [60, 109, 150, 4] | Normalize feature maps |
| Max Pool | — | [60, 36, 50, 4] | 3 × 3 max-pooling |
| Convolutional Layer 2 | | | |
| Conv 2.1 | 296 | [60, 36, 50, 8] | 8 2D feature maps |
| BN + ReLU | 32 | [60, 36, 50, 8] | Normalize feature maps |
| Conv 2.2 | 584 | [60, 36, 50, 8] | 8 2D feature maps |
| BN + ReLU | 32 | [60, 36, 50, 8] | Normalize feature maps |
| Max Pool | — | [60, 12, 16, 8] | 3 × 3 max-pooling |
| Convolutional Layer 3 | | | |
| Conv 3.1 | 1,168 | [60, 12, 16, 16] | 16 2D feature maps |
| BN + ReLU | 64 | [60, 12, 16, 16] | Normalize feature maps |
| Conv 3.2 | 2,320 | [60, 12, 16, 16] | 16 2D feature maps |
| BN + ReLU | 64 | [60, 12, 16, 16] | Normalize feature maps |
| Max Pool | — | [60, 4, 5, 16] | 3 × 3 max-pooling |
| LSTM Layers | | | |
| Flatten | — | [60, 320] | Reshape to vectors |
| LSTM 1 | 10,528 | [60, 8] | 60 step LSTM |
| LSTM 2 | 208 | [4] | Last state LSTM |
| Output Layer | | | |
| Dropout | — | [4] | 50% Dropout |
| Dense + Sigmoid | 5 | [1] | Logit to Output |

TABLE 12

| Layer | # Parameters | Output Shape | Description |
|---|---|---|---|
| Convolutional Layer 1 | | | |
| Conv 1.1 | 40 | [60, 109, 150, 4] | 4 2D feature maps |
| BN + ReLU | 16 | [60, 109, 150, 4] | Normalize feature maps |
| Conv 1.2 | 148 | [60, 109, 150, 4] | 4 2D feature maps |
| BN + ReLU | 16 | [60, 109, 150, 4] | Normalize feature maps |
| Max Pool | — | [60, 36, 50, 4] | 3 × 3 max-pooling |
| Convolutional Layer 2 | | | |
| Conv 2.1 | 296 | [60, 36, 50, 8] | 8 2D feature maps |
| BN + ReLU | 32 | [60, 36, 50, 8] | Normalize feature maps |
| Conv 2.2 | 584 | [60, 36, 50, 8] | 8 2D feature maps |
| .BN + ReLU | 32 | [60, 36, 50, 8] | Normalize feature maps |
| Max Pool | — | [60, 12, 16, 8] | 3 × 3 max-pooling |
| Convolutional Layer 3 | | | |
| Conv 3.1 | 1,168 | [60, 12, 16, 16] | 16 2D feature maps |
| BN + ReLU | 64 | [60, 12, 16, 16] | Normalize feature maps |
| Conv 3.2 | 2,320 | [60, 12, 16, 16] | 16 2D feature maps |
| BN + ReLU | 64 | [60, 12, 16, 16] | Normalize feature maps |
| Max Pool | — | [60, 4, 5, 16] | 3 × 3 max-pooling |
| Output Layer | | | |
| GAP | — | [16] | Global average Pooling |
| Dropout | — | [16] | 50% Dropout |
| Dense + Sigmoid | 17 | [1] | Logit to Output |

TABLE 13

| Layer | # Parameters | Output Shape | Description |
|---|---|---|---|
| Convolutional Layer 1 | | | |
| Conv 1.1 | 112 | [60, 109, 150, 4] | 4 3D feature maps |
| BN + ReLU | 16 | [60, 109, 150, 4] | Normalize feature maps |
| Conv 1.2 | 436 | [60, 109, 150, 4] | 4 3D feature maps |
| BN + ReLU | 16 | [60, 109, 150, 4] | Normalize feature maps |
| Max Pool | — | [20, 36, 50, 4] | 3 × 3 × 3 max-pooling |
| Convolutional Layer 2 | | | |
| Conv 2.1 | 872 | [20, 36, 50, 8] | 8 3D feature maps |
| BN + ReLU | 32 | [20, 36, 50, 8] | Normalize feature maps |
| Conv 2.2 | 1,736 | [20, 36, 50, 8] | 8 3D feature maps |
| BN + ReLU | 32 | [20, 36, 50, 8] | Normalize feature maps |
| Max Pool | — | [6, 12, 16, 8] | 3 × 3 max-pooling |
| Convolutional Layer 3 | | | |
| Conv 3.1 | 3,472 | [6, 12, 16, 16] | 16 3D feature maps |
| BN + ReLU | 64 | [6, 12, 16, 16] | Normalize feature maps |
| Conv 3.2 | 6,928 | [6, 12, 16, 16] | 16 3D feature maps |
| BN + ReLU | 64 | [6, 12, 16, 16] | Normalize feature maps |
| Max Pool | — | [2, 4, 5, 16] | 3 × 3 max-pooling |
| Output Layer | | | |
| Flatten | — | [640] | Reshape to vector |
| Dropout | — | [640] | 50% Dropout |
| Dense + Sigmoid | 641 | [1] | Logit to Output |

TABLE 14

| Layer | # Parameters | Output Shape | Description |
|---|---|---|---|
| Convolutional Layer 1 | | | |
| Conv 1.1 | 112 | [60, 109, 150, 4] | 4 3D feature maps |
| BN + ReLU | 16 | [60, 109, 150, 4] | Normalize feature maps |
| Conv 1.2 | 436 | [60, 109, 150, 4] | 4 3D feature maps |
| BN + ReLU | 16 | [60, 109, 150, 4] | Normalize feature maps |
| Max Pool | — | [20, 36, 50, 4] | 3 × 3 × 3 max-pooling |
| Convolutional Layer 2 | | | |
| Conv 2.1 | 872 | [20, 36, 50, 8] | 8 3D feature maps |
| BN + ReLU | 32 | [20, 36, 50, 8] | Normalize feature maps |
| Conv 2.2 | 1,736 | [20, 36, 50, 8] | 8 3D feature maps |
| BN + ReLU | 32 | [20, 36, 50, 8] | Normalize feature maps |
| Max Pool | — | [6, 12, 16, 8] | 3 × 3 max-pooling |

TABLE 14-continued

| Layer | # Parameters | Output Shape | Description |
|---|---|---|---|
| Convolutional Layer 3 | | | |
| Conv 3.1 | 3,472 | [6, 12, 16, 16] | 16 3D feature maps |
| BN + ReLU | 64 | [6, 12, 16, 16] | Normalize feature maps |
| Conv 3.2 | 6,928 | [6, 12, 16, 16] | 16 3D feature maps |
| BN + ReLU | 64 | [6, 12, 16, 16] | Normalize feature maps |
| Max Pool | — | [2, 4, 5, 16] | 3 × 3 max-pooling |
| Output Layer | | | |
| GAP | — | [16] | Global average Pooling |
| Dropout | — | [16] | 50% Dropout |
| Dense + Sigmoid | 17 | [1] | Logit to Output |

In testing, the convolutional units of the 2D and 3D CNNs were defined as a sequence of seven layers in the following composition: CNN layer, Batch Normalization, ReLU, CNN layer, Batch Normalization, ReLU, and Max Pooling. All kernel dimensions were set to 3 and Max Pooling was applied in a 3×3 window for 2D kernels and 3×3×3 for 3D kernels. Four additional versions were added by increasing the kernel sizes from 3 to 5 pixels in all dimensions, resulting in a total of eight candidate video models per echocardiography view.

Generally, the models 300, 304, 400, 404 are low parameter designs. The low parameter design was chosen due to the high computational cost of the presented experiments and to reduce the chance of overfitting. The 2D CNN+LSTM (e.g., the first model 300) consisted of a 2D CNN branch distributed to all frames of the video. This architecture was used for a video description problem, where all frames from a video belonged to the same scene or action. It is therefore assumed that static features would be commonly found by the same 2D kernels across the video. This assumption was put in practice for echocardiography view classification. The LSTM layer aggregates the CNN features over time to output a vector that represents the entire sequence.

The 2D CNN+GAP approach (e.g., the second model 304) exchanged the LSTM layers for the average CNN features as a time aggregation of frames. The GAP layer provided two advantages: it required no trainable parameters, saving 10,736 parameters from the LSTM layers, and it enabled feature interpretation. The final fully connected layer after the GAP provided a weighted average of the CNN features, which could indicate what sections of the video were weighted more in the final decision. The 3D CNN approach aggregated time and space features as the input data flowed through the network.

As opposed to the 2D CNN approach, a 3D CNN incorporated information from adjacent frames at every layer, extracting spatiotemporal dependent features which have also proven to be useful for video classification. In a 3D CNN approach, a GAP layer reduced the fully connected layer input from the feature map size to the number of filters. Thus, the GAP layer also reduced the number of parameters from 641 to 17.

As described above, a low parameter design was chosen due to the high computational cost of the presented experiments and to reduce the chance of overfitting. To complete all experiments, a total of 1,152 neural network models (24 views×5 folds×8 models for the cross-validations experiments plus 24 views×8 models for the final versions) were fit, which fully occupied all sixteen GPUs in a NVIDIA DGX2 for approximately forty days. Deep learning models typically consist of millions of parameters. For example the Inception model has twenty-five million parameters and ResNet more than forty million parameters, rendering the computational cost to train such large networks as prohibitive and, given the performance demonstrated in the disclosed models, potentially unnecessary. Even a relatively large disclosed model included less than 20,000 parameters.

In some embodiments, the models can be implemented using the docker container tensorflow:19.08py3 (available at nvcr.io/nvidia/) with Python version 3.6.8, Tensorflow module version 1.14, and Keras module version 2.2.4tf.

Cross-Validation Procedure

Using the cross-validation set described in Table 10 above, the echocardiography studies were split into five folds, where, at each of the five iterations, a fold was used for testing and the rest for training. Two constraints were enforced on the folds content: 1) studies from the same patient could not be present in more than one fold, and 2) each fold contained the similar positive prevalence (of 1-year all-cause mortality) as the entire dataset. For each training set, a tenth of the studies were set aside, with a balanced prevalence, as a proxy to the test set for internal validation. As the DNN was trained, the loss (binary cross-entropy) was evaluated on the internal validation set at each epoch. If the internal validation loss did not decrease for more than 10 epochs, the training was stopped and the model weights were recovered at the minimum validation loss.

All video architectures were trained on all available views in the training set. For each view, the architecture with the highest AUC was chosen in the internal validation set and that model was used to report performance for that view in all subsequent experiments. A summary of the architectures chosen for each view is presented Table 15, and an example for the PL DEEP view is presented in Table 16. EHR-derived features and video risk scores were concatenated for each view to fit a classification pipeline composed of an interquartile range scaler, a multivariate imputation by chained equations, and an XGboost classifier. This pipeline was fit at each training fold and applied to its corresponding test set to produce the output risk score.

Since the mortality prevalence in the overall dataset was imbalanced (14.6% of patients died within a year of the echocardiography study), the weights for each class were set as follows:

$$w_i = \frac{\text{Total Number of Samples}}{2(\text{Number of Samples in class } i)}. \quad (2)$$

In testing, all training was performed on an NVIDIA DGX2 platform by independently fitting each model on each of the sixteen available GPUs.

TABLE 15

|  | Correct | | Change | | Accuracy | | Sensitivity | | Specificity | |
| --- | --- | --- | --- | --- | --- | --- | --- | --- | --- | --- |
|  | Solo | +DNN | + | − | Solo | +DNN | Solo | +DNN | Solo | +DNN |
| Cardiologist 1 | 416 | 456 | 65 | 25 | 69% | 76% | 61% | 71% | 78% | 81% |
| Cardiologist 2 | 392 | 442 | 80 | 30 | 65% | 74% | 49% | 66% | 82% | 81% |
| Cardiologist 3 | 387 | 427 | 65 | 25 | 65% | 71% | 42% | 56% | 87% | 87% |
| Cardiologist 4 | 374 | 400 | 39 | 13 | 62% | 67% | 41% | 53% | 83% | 80% |
| AC Score | 401 | 451 | 71 | 21 | 67% | 75% | 53% | 70% | 80% | 80% |

15

TABLE 16

|  | All (n = 3,384) | HFrEF (n = 2,026) | HFpEF (n = 1,357) |
| --- | --- | --- | --- |
| Seattle HF score | 0.70 [0.68, 0.71] | 0.70 [0.67, 0.72] | 0.69 [0.66, 0.72] |
| DNN model (full) | 0.76 [0.74, 0.77] | 0.76 [0.74, 0.78] | 0.75 [0.72, 0.78] |

Statistical Analysis

In all survival analyses, time to death or last known living encounter (censored) from the echocardiography study and the predicted labels were used to stratify the probability of survival for the Kaplan-Meier plots and Cox Proportional Hazard Ratio analysis. The analysis was conducted using the lifelines python package version 0.25.4. The thresholds for both the DNN and SHF models were chosen as the midpoint in the score range.

For the cross-validation experiment where an AUC estimate was per fold was obtained, the average across the 5 folds and 95% CI computed with $\pm 1.96\sigma/\sqrt{5}$ was reported.

For the remaining experiments where only a single AUC was available (Heart Failure and survey cohorts), the AUC estimation was bootstrapped for 10,000 iterations and reported the 2.5th and 97.5th percentiles as the 95% CI.

To report significant differences when comparing the predictive performance with the paired survey data, paired proportion tests were conducted on the number of correct answers out of the three hundred samples. A total of four tests comparing each of the four cardiologists to the DNN model were conducted, hence the p-value corrected threshold of 0.05/4. For the statistical computations, the statsmodel package for Python version 0.11.1 was used.

Seattle Heart Failure Implementation

An SHF score was calculated with typical parameters, with the exception that systolic blood pressure, hemoglobin, percentage of white blood cells in the form of lymphocytes, uric acid, total cholesterol, and sodium were defined as the most recent available measurement before (within a year) or the day of the echocardiogram, instead of using a potentially closer measurement in the future. For predicting future events both the DNN and SHF models were blinded to data collected after the date that the echocardiogram was acquired.

Heart Failure Subtype Definition

Heart failure type (i.e., reduced vs. preserved ejection fraction) was determined for each sample using all previous available ejection fraction measurements up to 6 months prior to heart failure diagnosis as follows: 1) heart failure with reduced ejection fraction (HFrEF) if any LVEF50%; 2) heart failure with preserved ejection fraction (HFpEF) if all LVEFs≥50%; 3) no subtype was assigned if no LVEF was ever reported.

Performance Assessment

First, the DNN model was cross-validated on a clinically-acquired echocardiography video database (812,278 videos). Independent models were trained for individual views (parasternal long-axis, apical 4-chamber, etc.) and aggregated to form a feature vector that consisted of the outputs from individual view models. On average, using all echocardiography video views combined yielded higher performance (area under the receiver operating characteristic curve (AUC): 0.83, 95% CI) for predicting 1-year mortality than using either 58 EDM (AUC: 0.75, 95% CI) or the combination of the 58 EDM and 100 additional clinical variables from the EHR including relevant cardiovascular-related diagnoses, lab values, demographics and vital signs (AUC: 0.81, 95% CI). The largest model that combined all views and the 158 EHR-derived measurements yielded an AUC of 0.84, 95% CI. Individual view models ranged in performance from AUC of 0.700.80, with parasternal long-axis views producing the best individual performance. Finally, a PCE score, a clinical standard benchmark for future cardiovascular disease, was calculated for the same samples. The PCE score yielded an AUC of 0.64 (95% CI) for 1-year mortality prediction, which was inferior to all DNN models tested.

Given this proof-of-concept from the cross-validation experiments for predicting 1-year mortality from echocardiography videos with a DNN, the DNN models were retrained using all 812,278 videos from the cross-validation experiments, and evaluated performance on two new and distinct groups of patients. The first group was an independent set of 600 patients (survey set), balanced for the 1-year mortality outcome (i.e. three hundred patients who survived for 1 year after echocardiography and three hundred patients who died within 1 year). The second group was a cohort of 2,404 patients with heart failure (defined as "definite" heart failure by eMERGE guidelines) who underwent 3,384 echocardiograms.

The survey set was used to evaluate the performance of four expert cardiologists, three Core Cardiovascular Training Statement (COCATS) level 3 and one level 2 in echocardiography. The cardiologists were independently and blindly asked to determine whether each patient would be alive or dead at 1 year following the echocardiogram. For the sake of assessing the cardiologists' performances in an efficient manner, a limited input set of a single video from the parasternal long-axis view (the highest-performing individual view) and 10 EHR variables were presented to compare their performance with a model trained on the same input set. A risk score from the cardiologists' answers was constructed by aggregating the number of positive predictions (deceased within 1 year) for each patient. The DNN model yielded an AUC of 0.84, 95% CI, while the aggregated cardiologist score yielded an inferior AUC of 0.68, 95% CI.

To further evaluate the performance of the DNN model compared to cardiologists, the survey set was rearranged to show matched pairs. No individual-level feedback was provided to the cardiologists between experiments. In this second survey, the cardiologists and the model were presented with two studies at a time: one study was from a patient who died within one year and the other was from a patient who lived beyond 1 year of the echocardiogram. Both the cardiologists and the model were asked to select the patient from each pair with the higher chance of death at 1 year. Three hundred pairs were matched by sex, age (within 5 years), and left ventricular ejection fraction (EF) (within 10% absolute difference). This survey was designed to control for the outcome prevalence and directly measure discrimination performance. The DNN model yielded an accuracy of 82%, while the four cardiologists scored 66, 70, 73, and 76%. It is noted that simple heuristics, such as selecting the older patient or the lower EF as the positive sample resulted in 43% (131 samples) and 36% (108 samples) accuracy, respectively. Using a paired proportion test, the model yielded significantly higher performance than three out of four cardiologists after correcting for multiple comparisons (p<0.05/4).

Next, it was evaluated whether the cardiologists could improve their performance when assisted by the model. Similar to the first survey, a single study was shown at a time, collected the cardiologist prediction, and then immediately presented the same study along with the machine prediction score. The aggregated cardiologist score AUC improved from 0.72, 95% CI, to 0.78, 95% CI with assistance from the model predictions, which marginally overlaps with the DNN performance. In the survey, on average, the cardiologists correctly changed 10.3% of their predictions and incorrectly changed in 3.8% of their predictions. Sensitivity increased by 13% while specificity reduced less than 1% on average.

The second group of patients in which the fully-trained DNN model (All Views+EHR) was applied was a cohort of 2,404 patients with heart failure (defined as "definite" heart failure by eMERGE guidelines) who underwent 3,384 echocardiograms. This group of patients was chosen as an important additional clinical validation since heart failure is prevalent and costly and the management of heart failure relies heavily on survival prediction models such as the SHF risk score. Within this cohort, the SHF score yielded an AUC of 0.70, 95% CI, while the DNN model yielded an AUC of 0.76, 95% CI. Notably, this superior performance of the DNN was observed for patients with both reduced (HFrEF) and preserved EF (HFpEF), see Table 16.

Predictions were computed based on a midrange threshold for the DNN model (0.5) and the SHF score (1.5) to discriminate between high and low risk. The range of scores was 0 to 1 for the DNN model and 1 to 4 for the SHF model.

Finally, which features the DNN model was learning from the echocardiography videos was investigated. To do this, sample videos were occluded with 10×10×10 three-dimensional voxels and the difference in the likelihood score that resulted from occluding that particular region was calculated. Since the results of the occlusion are videos, the first frame and overlaid red regions are displayed to denote significant changes in risk score (>2.5 standard deviations) for at least ten frames. These occlusion experiments for four patients with the highest prediction score who died within one year and four patients with the lowest prediction score who survived beyond 1 year. These patients were selected from the test set of the first cross-validation experiment fold. Note that for the high-risk patients, the occlusion decreases the risk score while for the low risk patients, the occlusion increases the risk score. Generally, it was observed that the most impactful regions coincided with anatomically relevant regions of the heart, particularly the left atrium, left ventricle, and the mitral and aortic valve planes. These regions appeared to be more limited and localized in the lower risk videos, whereas the higher risk videos appeared to additionally leverage surrounding anatomy; however, when presenting several examples of the occlusion maps to cardiologists, they anecdotally reported that they were unable to identify patterns that could help them better discern patient survival outcomes.

In summary, the ability for neural networks to assist physicians with an important clinical task of predicting 1-year all-cause mortality has been demonstrated. The ability of the DNN model to discriminate 1-year mortality surpassed that of models leveraging only image-derived and standard clinical measurements from the EHR as well as multiple existing clinical risk scores. Moreover, the DNN model enhanced the predictive performance of four trained cardiologists. This echocardiography video-based DNN model can therefore add value beyond a standard clinical interpretation.

Survival was chosen as a highly important, unambiguous clinical outcome, and other outcomes such as PFS can be used. Even when observer variability in echocardiography may exist for predicting human-defined outcomes, the use of mortality labels can help to minimize, if not eliminate, this challenge. Improving predictive performance may directly improve patient risk assessment prior to elective surgical procedures or impact therapy guidance for both primary and secondary prevention of cardiovascular disease in the outpatient setting. Also, at the population level, an improved mortality risk model may enable health systems and insurance providers to better understand and optimally deploy resources to their patient population, as demonstrated previously using only EHR variables in patients with heart failure. For heart failure in particular, methods for determining patient candidacy for advanced therapies such as cardiac transplant and implantation of durable mechanical support devices historically rely on mortality risk assessments based partly on peak oxygen consumption and invasive hemodynamics. Consideration for defibrillator placement in patients with heart failure is also predicated on a reasonable expectation of meaningful survival for more than 1 year. Implementation of a more accurate mortality-based risk tool may have additive benefit. Finally, estimation of 1-year mortality is particularly important for planning the transition to palliative care and hospice. Further research will be needed to evaluate the performance of neural network models to predict additional clinically relevant outcomes in cardiology such as future hospitalizations or the need for major procedures like a valve replacement.

Figure 19:
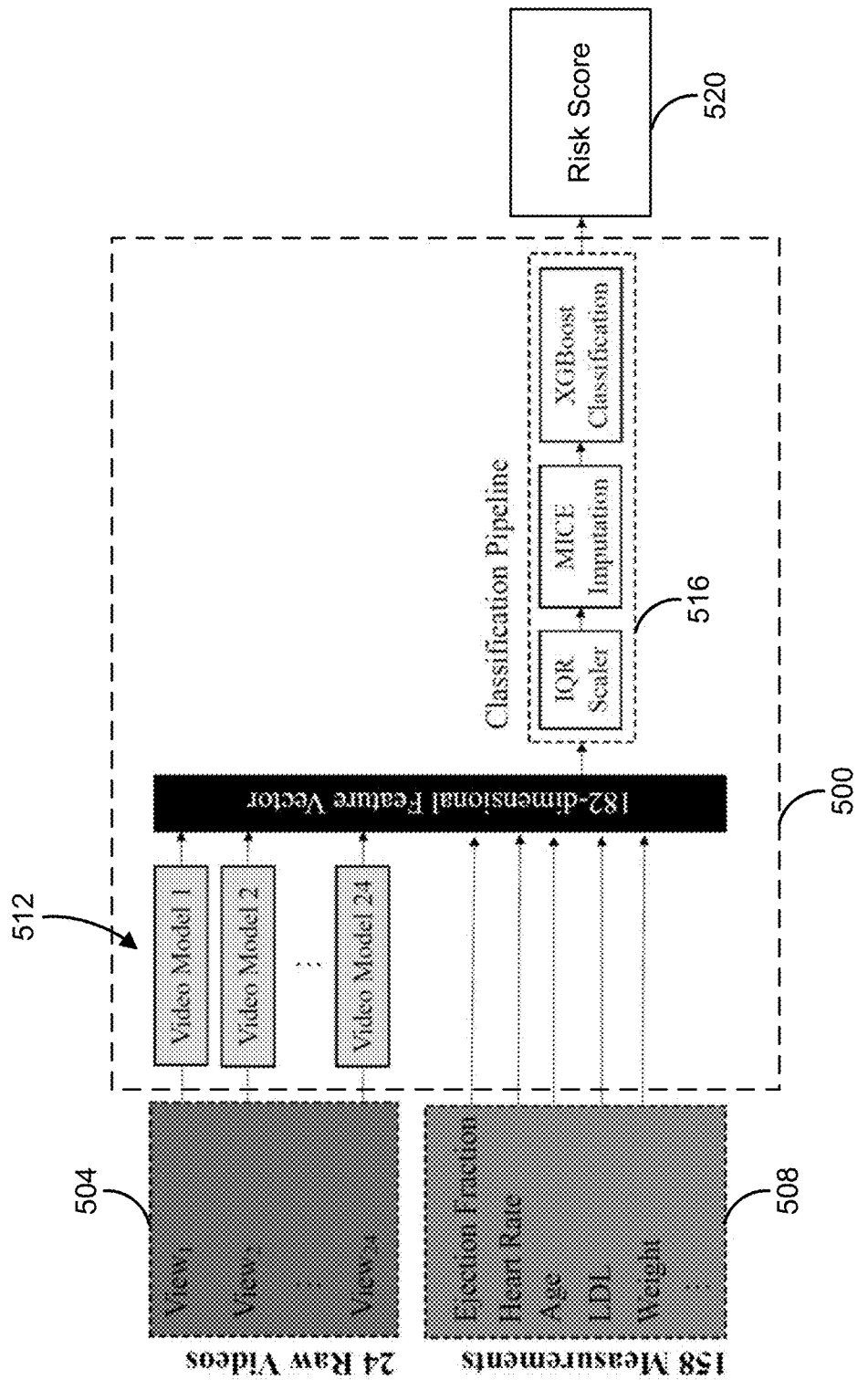
FIG. 19 is an exemplary trained model.

Referring now to FIG. 19, an exemplary trained model 500 is shown. In some embodiments, the model 500 can receive at least one echocardiogram video 504 and/or EHR data 508 associated with a patient. In some embodiments, the HER information can include values of a number of patient parameters, such as the parameters in Table 3. In some embodiments, the model 500 can include a number of trained video models 512. Each video model included in the number of trained video models 512 can be associated with an echocardiogram view. In some embodiments, each video model included in the number of trained video models 512 can be associated with a unique echocardiogram view included in Table 9 and/or Table 4. In some embodiments, the number of trained video models 512 can include the first model 300, the second model 304, the third model 400, and/or the fourth model 404. Each trained model included in the trained video models 512 can be selected by determining the best performing (e.g., highest AUC) model architecture for each echocardiographic view. For example, for a first echocardiographic view, the first model 300 may be the best, and for a second echocardiographic view, the fourth model 404 may be the best.

In some embodiments, the trained model 500 can receive the at least one echocardiogram video 504, provide each echocardiogram video in the at least one echocardiogram video 504 to a trained video model included in the number of trained video models 512, and receive a risk score (e.g., a video risk score) from each of the number of trained video models 512. In some embodiments, the trained model 500 can provide each risk score and/or the EHR data 508 to a trained submodel 516. In some embodiments, the trained submodel 516 can receive each risk score and/or the EHR data 508 and generate an output value, such as a mortality risk score 520 (e.g., an all-causes mortality risk score) and/or a progression-free survival score.

Figure 20:
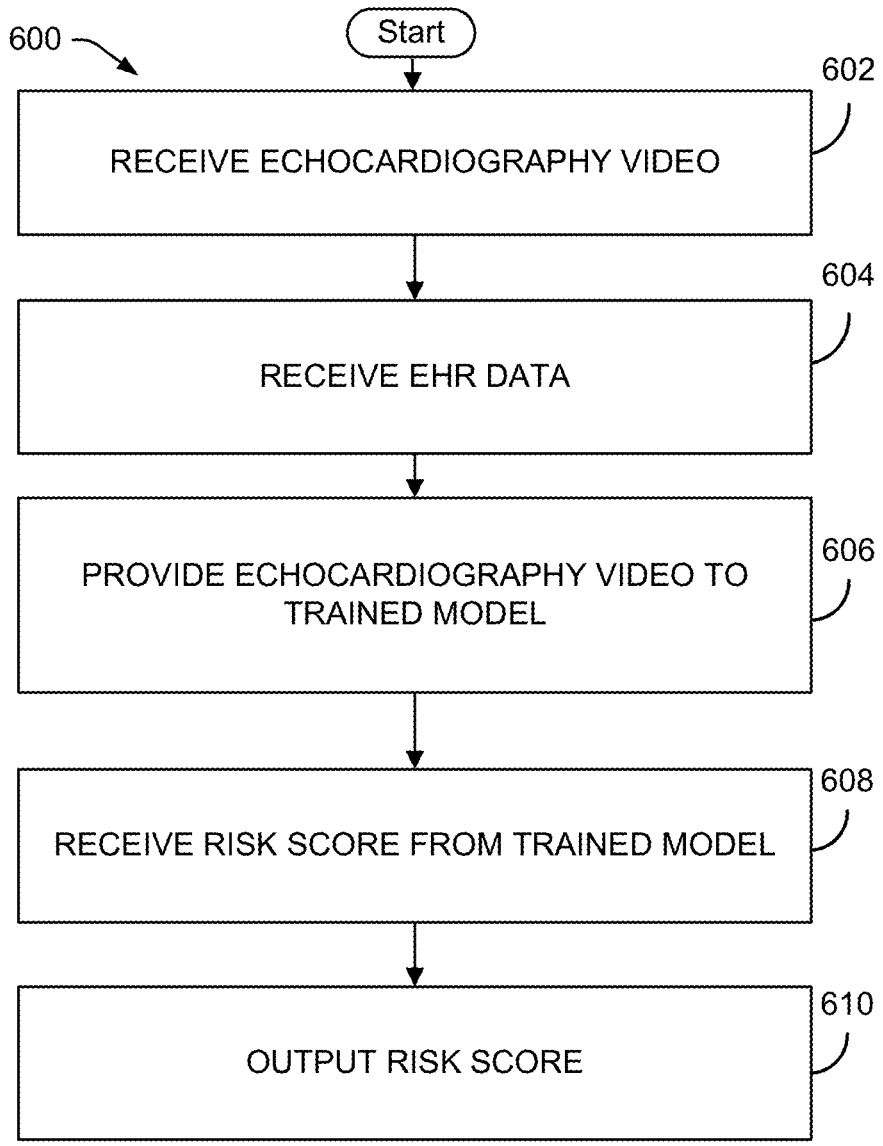
FIG. 20 is another exemplary process for predicting a relevant clinical endpoint such as all-cause mortality in a patient for a predetermined time period.

Referring now to FIG. 20, another exemplary process 600 for predicting a relevant clinical endpoint such as all-cause mortality in a patient for a predetermined time period (i.e., one year) based on a video of the heart (in this case echocardiography data) as well as any additional available EHR data is shown. In some embodiments, the process 600 can a risk score for the patient based on a neural network, which can be a deep neural network such as a convolutional neural network, trained using videos of the heart such as echocardiogram videos and EHR variables as described above. In some embodiments, the process 600 can be employed in a health analytics module that is used by a care team including the physician in order to treat the patient or for population level management of patients, for example a physician deploying resources to an entire population of ten thousand patients with heart failure. In some embodiments, the process 600 can be implemented as instructions (e.g., computer readable instructions) on at least one memory, and executed by one or more processors coupled to the at least one memory.

At 602, the process 600 can receive a number of echocardiographic videos of a heart associated with a patient. Each echocardiographic video can include echocardiography video frames. The video frames can include video frames taken from one or more views of the heart of the patient. For example, the video frames can include video frames taken at twenty-one different views of the heart. In some embodiments, the echocardiographic video can be associated with one or more echocardiographic views including an apical two-chamber view, an apical three-chamber view, an apical four-chamber view, an apical four-chamber focused to right ventricle view, an apical five chamber view, a parasternal long axis view, a parasternal long descending aorta view, a parasternal long mitral valve view, a parasternal long pulmonic valve view, a parasternal long right ventricle inflow view, a parasternal long zoom aortic valve view, a parasternal short aortic valve view, a parasternal short pulmonic valve and pulmonary artery view, a parasternal short tricuspid valve view, a short axis apex view, a short axis base view, a short axis mid papillary view, a subcostal four-chamber view, a subcostal hepatic vein view, a subcostal inter-atrial septum view, a subcostal inferior vena cava view, a subcostal right ventricle view, a suprasternal notch view, a short axis mid papillary view, a short axis apex view, an apical three-chamber zoom view, an apical two-chamber zoom view, and/or a short axis base view. The process 600 can then proceed to 604.

At 604, the process 600 can receive EHR data including a number of values of parameters associated with the patient. In some embodiments, 604 can be substantially the same as 104 in FIG. 12. The process 600 can then proceed to 606.

At 606, the process 600 can provide the number of echocardiographic videos and the EHR data to a trained model. In some embodiments, the trained model can be the model 500 in FIG. 19. In some embodiments, the process 600 can provide each echocardiographic video to an associated trained video model included in the trained model (e.g., a trained video model associated with the same echocardiographic view as the video). In some embodiments, the process 600 can provide the EHR data to a trained submodel (e.g., the submodel 516 in the model 500) along with risk scores (video risk scores) generated by the trained video models based on the echocardiographic videos. At 606, the process 600 can analyze one or more regions of the heart using the trained model. In some embodiments, the process 600 can analyze one or more regions of the heart including a left atrium, a left ventricle, a mitral valve, and/or an aortic valve. The process 600 can then proceed to 608.

At 608, the process 600 can receive a risk score from the trained model. In some embodiments, risk score can be the risk score 520 in FIG. 19. In some embodiments, the risk score can be a mortality risk score. In some embodiments, the risk score can be a progression-free survival score. The process 600 can then proceed to 610.

At 610, the process 600 can output the raw risk score to at least one of a memory or a display for viewing by a medical practitioner or healthcare administrator. In some embodiments, the process 600 can generate and output a report based on the risk score. The report can include the raw risk score. The report can include any appropriate graphs and/or charts generated based on the risk score. The report can be displayed to a physician using a display such as a computer monitor or a screen integral to a tablet computer, smartphone, laptop computer etc. In some embodiments, the report can be output to a storage device including a memory. In some embodiments, the report can include information about potential treatments for the patient and/or links to information about the potential treatments for the patient. In some embodiments, the links can be hyperlinks. In some embodiments, the potential treatments for the patient can include cardiac transplantation, implantation of mechanical support devices, defibrillator placement, palliative care, and/or hospice. In some embodiments, a medical practitioner may make a determination (e.g., an eligibility determination) for the patient based on the report.

In conclusion, a methodology and architecture for extracting clinically-relevant predictive information from medical videos with a deep neural network is disclosed.

Thus, as described herein, the present disclosure provides systems and methods for efficiently and accurately analyzing videos of a heart such as videos acquired during an echocardiogram in order to assist physicians in assessing heart anatomy and function and predicting future clinical events.

While the present disclosure may be susceptible to various modifications and alternative forms, specific embodiments have been shown by way of example in the drawings and have been described in detail herein. However, it should be understood that the present disclosure is not intended to be limited to the particular forms disclosed. Rather, the present disclosure is to cover all modifications, equivalents, and alternatives falling within the spirit and scope of the present disclosure as defined by the following appended claims.

This written description uses examples to disclose the present disclosure, including the best mode, and also to enable any person skilled in the art to practice the present disclosure, including making and using any devices or systems and performing any incorporated methods. The patentable scope of the present disclosure is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Finally, it is expressly contemplated that any of the processes or steps described herein may be combined, eliminated, or reordered. Accordingly, this description is meant to be taken only by way of example, and not to otherwise limit the scope of this present disclosure.

What is claimed is:

1. A method comprising:
    receiving an echocardiographic video of a heart associated with a patient;
    providing the echocardiographic video to a trained neural network, the trained neural network being trained to generate a mortality risk score based on input echocardiographic video;
    receiving a mortality risk score associated with the patient from the trained neural network; and
    outputting the mortality risk score associated with the patient to at least one of a memory or a display for viewing by a medical practitioner or healthcare administrator,
    wherein the trained neural network includes at least a first layer and a second layer, the first layer trained to generate, based on input echocardiographic video having first video dimensions, a first layer output having output dimensions that are different from the first video dimensions, and the second layer trained to generate, at least partially based on the first layer output, a mortality risk score.

2. The method of claim 1, wherein the mortality risk score associated with the patient is indicative of a likelihood the patient will die within a predetermined period of time from when the echocardiographic video was generated.

3. The method of claim 2, wherein the mortality risk score associated with the patient is indicative of a likelihood the patient will die from all causes within the predetermined period of time.

4. The method of claim 1, wherein the trained neural network is trained based on a training dataset comprising a plurality of videos, each video of the plurality of videos being associated with an echocardiographic view selected from among a number of echocardiographic views, at least a portion of the training dataset being associated with definite heart failure in accordance with cMERGE.

5. The method of claim 4, wherein the training dataset further comprises an electronic health record dataset, each video of the plurality of videos being associated with a portion of the electronic health record dataset.

6. The method of claim 5, wherein the electronic health record dataset is associated with a number of patients and comprises values of a number of parameters including age, tricuspid regurgitation maximum velocity, heart rate, low density lipoprotein, left ventricular ejection fraction, diastolic pressure, pulmonary artery acceleration time, systolic pressure, pulmonary artery acceleration slope, and diastolic function.

7. The method of claim 5, wherein the electronic health record dataset comprises values of a number of parameters including demographic parameters, vitals parameters, laboratory measurement parameters, echocardiogram-based parameters, and diagnosis parameters.

8. The method of claim 7, wherein the demographic parameters comprise age, sex, and smoking status.

9. The method of claim 7, wherein the vitals parameters comprise height, weight, heart rate, diastolic blood pressure, and systolic blood pressure.

10. The method of claim 7, wherein the laboratory measurement parameters comprise low-density lipoprotein level and high-density lipoprotein level.

11. The method of claim 7, wherein the echocardiogram-based parameters comprise:
    physician-reported left ventricular ejection fraction,
    aortic insufficiency deceleration slope,
    aortic insufficiency maximum velocity,
    velocity-time integral of distal to aortic valve flow,
    maximum velocity of distal to aortic valve flow,
    mean velocity of distal to aortic valve flow,
    aortic root diameter,
    ascending aortic diameter,
    lv end-diastolic volume: apical 2-chamber; modified ellipsoid,
    lv end-diastolic volume: apical 4-chamber; modified ellipsoid,
    lv end-diastolic volume: apical 2-chamber; single plane,
    lv end-diastolic volume: apical 4-chamber; single plane,
    lv end-systolic volume: apical 2-chamber; modified ellipsoid,
    lv end-systolic volume: apical 4-chamber; modified ellipsoid,
    lv end-systolic volume: apical 2-chamber; single plane,
    lv end-systolic volume: apical 4-chamber; single plane,
    iv septum dimension at end-diastole,
    left atrium dimension,
    left atrium volume derived from apical 2-chamber; modified ellipsoid,
    left atrium volume derived from apical 4-chamber; modified ellipsoid,
    velocity-time integral proximal to the obstruction,
    maximum lv velocity proximal to the obstruction,
    mean lv velocity proximal to the obstruction,
    lv area at end-diastole derived from apical 2-chamber,
    lv area at end-diastole derived from apical 4-chamber,
    lv area at end-systole derived from apical 2-chamber,
    lv area at end-systole derived from apical 4-chamber, lv internal dimension at end-diastole,
lv internal dimension at end-systole,
lv long-axis length at end-diastole derived from apical 2-chamber,
lv long-axis length at end-diastole derived from apical 4-chamber,
lv long-axis length at end systole derived from apical 2-chamber,
lv long-axis length at end systole derived from apical 4-chamber,
lv outflow tract area,
lv outflow tract diameter,
lv posterior wall thickness at end-diastole,
mitral regurgitation maximum velocity,
a-point maximum velocity of mitral flow,
e-point maximum velocity of mitral flow,
maximum velocity of mitral valve flow,
mitral valve deceleration slope,
mitral valve deceleration time,
maximum velocity of distal to pulmonic valve flow,
pulmonary artery acceleration slope,
pulmonary artery acceleration time,
pulmonary r-r time interval,
right atrial end-systolic mean pressure,
right ventricle dimension at end-diastole,
tricuspid regurgitation maximum velocity,
aortic valve regurgitation,
mitral valve regurgitation,
tricuspid valve regurgitation,
pulmonary valve regurgitation,
aortic valve stenosis,
mitral valve stenosis,
tricuspid valve stenosis,
pulmonary valve stenosis, and
physician-reported diastolic function.

12. The method of claim 7, wherein the diagnosis parameters comprise: diagnosis of acute rheumatic fever, diagnosis of chronic rheumatic heart disease, diagnosis of hypertensive diseases, diagnosis of ischemic heart diseases, diagnosis of pulmonary heart disease and diseases of pulmonary circulation, diagnosis of acute pericarditis, diagnosis of other forms of heart disease, diagnosis of acute myocarditis, diagnosis of cardiomyopathy, diagnosis of cardiac arrest, diagnosis of paroxysmal tachycardia, diagnosis of atrial fibrillation, diagnosis of heart failure, diagnosis of cerebrovascular diseases, diagnosis of diseases of arteries, arterioles and capillaries, diagnosis of diseases of veins, lymphatic vessels, and lymph nodes, diagnosis of hypotension, diagnosis of other and unspecified disorders of the circulatory system, diagnosis of diabetes mellitus, diagnosis of congenital heart defect, diagnosis of dyslipidemia, and diagnosis of chronic kidney disease.

13. The method of claim 4, wherein the number of echocardiographic views comprises at least one echocardiographic view.

14. The method of claim 4, wherein the number of echocardiographic views comprises at least one of an apical two-chamber view, an apical three-chamber view, an apical four-chamber view, an apical four-chamber focused to right ventricle view, an apical five chamber view, a parasternal long axis view, a parasternal long descending aorta view, a parasternal long mitral valve view, a parasternal long pulmonic valve view, a parasternal long right ventricle inflow view, a parasternal long zoom aortic valve view, a parasternal short aortic valve view, a parasternal short pulmonic valve and pulmonary artery view, a parasternal short tricuspid valve view, a short axis apex view, a short axis base view, a short axis mid papillary view, a subcostal four-chamber view, a subcostal hepatic vein view, a subcostal inter-atrial septum view, a subcostal inferior vena cava view, a subcostal right ventricle view, a suprasternal notch view, a short axis mid papillary view, a short axis apex view, an apical three-chamber zoom view, an apical two-chamber zoom view, or a short axis base view.

15. The method of claim 4, wherein the training dataset further comprises a plurality of survival outcomes, each video of the plurality of videos being associated with a survival outcome included in the plurality of survival outcomes.

16. The method of claim 1 further comprising:
receiving electronic health record information associated with the patient; and
providing the electronic health record information to the trained neural network, the trained neural network being further trained to generate the mortality risk score based on input electronic health record information.

17. The method of claim 16, wherein the electronic health record information comprises values of a number of parameters including age, tricuspid regurgitation maximum velocity, heart rate, low density lipoprotein, left ventricular ejection fraction, diastolic pressure, pulmonary artery acceleration time, systolic pressure, pulmonary artery acceleration slope, and diastolic function, the values being associated with the patient.

18. The method of claim 16, wherein the electronic health record information comprises values of a number of parameters including demographic parameters, vitals parameters, laboratory measurement parameters, echocardiogram-based parameters, and diagnosis parameters.

19. The method of claim 18, wherein the demographic parameters comprise age, sex, and smoking status.

20. The method of claim 18, wherein the vitals parameters comprise height, weight, heart rate, diastolic blood pressure, and systolic blood pressure.

21. The method of claim 18, wherein the laboratory measurement parameters comprise comprising low-density lipoprotein level and high-density lipoprotein level.

22. The method of claim 18, wherein the echocardiogram-based parameters comprise physician-reported left ventricular ejection fraction, aortic insufficiency deceleration slope, aortic insufficiency maximum velocity, velocity-time integral of distal to aortic valve flow, maximum velocity of distal to aortic valve flow, mean velocity of distal to aortic valve flow, aortic root diameter, ascending aortic diameter, lv end-diastolic volume: apical 2-chamber; modified ellipsoid, lv end-diastolic volume: apical 4-chamber; modified ellipsoid, lv end-diastolic volume: apical 2-chamber; single plane, lv end-diastolic volume: apical 4-chamber; single plane, lv end-systolic volume: apical 2-chamber; modified ellipsoid, lv end-systolic volume: apical 4-chamber; modified ellipsoid, lv end-systolic volume: apical 2-chamber; single plane, lv end-systolic volume: apical 4-chamber; single plane, iv septum dimension at end-diastole, left atrium dimension, left atrium volume derived from apical 2-chamber; modified ellipsoid, left atrium volume derived from apical 4-chamber; modified ellipsoid, velocity-time integral proximal to the obstruction, maximum lv velocity proximal to the obstruction, mean lv velocity proximal to the obstruction, lv area at end-diastole derived from apical 2-chamber, lv area at end-diastole derived from apical 4-chamber, lv area at end-systole derived from apical 2-chamber, lv area at end-systole derived from apical 4-chamber, lv internal dimension at end-diastole, lv internal dimension at end-systole, lv long-axis length at end-diastole derived from apical 2-chamber, lv long-axis length at end-diastole derived from apical 4-, chamber, lv long-axis length at end systole derived from apical 2-, chamber, lv long-axis length at end systole derived from apical 4-chamber, lv outflow tract area, lv outflow tract diameter, lv posterior wall thickness at end-diastole, mitral regurgitation maximum velocity, a-point maximum velocity of mitral flow, e-point maximum velocity of mitral flow, maximum velocity of mitral valve flow, mitral valve deceleration slope, mitral valve deceleration time, maximum velocity of distal to pulmonic valve flow, pulmonary artery acceleration slope, pulmonary artery acceleration time, pulmonary r-r time interval, right atrial end-systolic mean pressure, right ventricle dimension at end-diastole, tricuspid regurgitation maximum velocity, aortic valve regurgitation, mitral valve regurgitation, tricuspid valve regurgitation, pulmonary valve regurgitation, aortic valve stenosis, mitral valve stenosis, tricuspid valve stenosis, pulmonary valve stenosis, and physician-reported diastolic function.

23. The method of claim 18, wherein the diagnosis parameters comprise diagnosis of acute rheumatic fever, diagnosis of chronic rheumatic heart disease, diagnosis of hypertensive diseases, diagnosis of ischemic heart diseases, diagnosis of pulmonary heart disease and diseases of pulmonary circulation, diagnosis of acute pericarditis, diagnosis of other forms of heart disease, diagnosis of acute myocarditis, diagnosis of cardiomyopathy, diagnosis of cardiac arrest, diagnosis of paroxysmal tachycardia, diagnosis of atrial fibrillation, diagnosis of heart failure, diagnosis of cerebrovascular diseases, diagnosis of diseases of arteries, arterioles and capillaries, diagnosis of diseases of veins, lymphatic vessels, and lymph nodes, diagnosis of hypotension, diagnosis of other and unspecified disorders of the circulatory system, diagnosis of diabetes mellitus, diagnosis of congenital heart defect, diagnosis of dyslipidemia, and diagnosis of chronic kidney disease.

24. The method of claim 1, wherein the echocardiographic video of the heart associated with the patient is associated with a single echocardiographic view.

25. The method of claim 24, wherein the single echocardiographic view is a parasternal long axis view.

26. The method of claim 1 further comprising:
generating a report based on the mortality risk score,
the report comprising at least one of information about potential treatments for the patient or links to information about the potential treatments for the patient,
the potential treatments for the patient comprising at least one of cardiac transplantation, implantation of mechanical support devices, defibrillator placement, palliative care, or hospice.

27. The method of claim 1, wherein the mortality risk score associated with the patient provides sufficient information to the medical practitioner or healthcare administrator for the medical practitioner or healthcare administrator to make a determination about a potential treatment for the patient, the potential treatment comprising at least one of cardiac transplantation, implantation of mechanical support devices, defibrillator placement, palliative care, or hospice.

28. The method of claim 27, wherein the determination is eligibility for the treatment.

29. A system, comprising:
at least one processor coupled to at least one memory comprising instructions, the at least one processor executing the instructions to:
receive an echocardiographic video of a heart associated with a patient;
provide the echocardiographic video to a trained neural network, the trained neural network being trained to generate a mortality risk score based on input echocardiographic video;
receive a mortality risk score associated with the patient from the trained neural network; and
output the mortality risk score associated with the patient to at least one of a memory or a display for viewing by a medical practitioner or healthcare administrator,
wherein the trained neural network includes at least a first layer and a second layer, the first layer trained to generate, based on input echocardiographic video having first video dimensions, a first layer output having output dimensions that are different from the first video dimensions, and the second layer trained to generate, at least partially based on the first layer output, a mortality risk score.

30. The system of claim 29, wherein the at least one processor further executes the instructions to:
receive electronic health record information associated with the patient; and
provide the electronic health record information to the trained neural network, the trained neural network being further trained to generate the mortality risk score based on input electronic health record information,
wherein the electronic health record information comprises values of a number of parameters including age, tricuspid regurgitation maximum velocity, heart rate, low density lipoprotein, left ventricular ejection fraction, diastolic pressure, pulmonary artery acceleration time, systolic pressure, pulmonary artery acceleration slope, and diastolic function.

* * * * *